US009958456B2

(12) United States Patent
Thiele et al.

(10) Patent No.: US 9,958,456 B2
(45) Date of Patent: May 1, 2018

(54) OXMIF AS A DIAGNOSTIC MARKER

(71) Applicants: Baxalta GmbH, Glattpark (Opfikon) (CH); Baxalta Incorporated, Bannockburn, IL (US)

(72) Inventors: Michael Thiele, Vienna (AT); Randolf J. Kerschbaumer, Klosterneuburg (AT); Dirk Voelkel, Vienna (AT); Patrice Douillard, Vienna (AT); Friedrich Scheiflinger, Vienna (AT)

(73) Assignees: Baxalta Incorporated, Bannockburn, IL (US); Baxalta GmbH, Zug (CH)

(*) Notice: Subject to any disclaimer, the term of this patent is extended or adjusted under 35 U.S.C. 154(b) by 0 days. days.

(21) Appl. No.: 14/350,186

(22) PCT Filed: Oct. 4, 2012

(86) PCT No.: PCT/EP2012/069598
§ 371 (c)(1),
(2) Date: Apr. 7, 2014

(87) PCT Pub. No.: WO2013/050453
PCT Pub. Date: Apr. 11, 2013

(65) Prior Publication Data
US 2014/0248638 A1    Sep. 4, 2014

Related U.S. Application Data

(60) Provisional application No. 61/545,042, filed on Oct. 7, 2011, provisional application No. 61/624,943, filed on Apr. 16, 2012, provisional application No. 61/668,841, filed on Jul. 6, 2012.

(51) Int. Cl.
*G01N 33/68* (2006.01)
*C07K 16/24* (2006.01)

(52) U.S. Cl.
CPC ......... *G01N 33/6863* (2013.01); *C07K 16/24* (2013.01); *G01N 2800/70* (2013.01)

(58) Field of Classification Search
None
See application file for complete search history.

(56) References Cited

U.S. PATENT DOCUMENTS

| | | | |
|---|---|---|---|
| 4,299,814 A | 11/1981 | Brandt et al. |
| 4,683,202 A | 7/1987 | Mullis |
| 4,708,937 A | 11/1987 | Remold |
| 4,946,674 A | 8/1990 | von Eichborn et al. |
| 4,946,778 A | 8/1990 | Ladner et al. |
| 5,350,687 A | 9/1994 | Odink et al. |
| 5,384,116 A | 1/1995 | Pawelek et al. |
| 5,411,882 A | 5/1995 | Odink et al. |
| 5,530,101 A | 6/1996 | Queen et al. |
| 5,559,028 A | 9/1996 | Humphreys |
| 5,585,479 A | 12/1996 | Hoke et al. |
| 5,726,020 A | 3/1998 | Humphreys et al. |
| 5,747,023 A | 5/1998 | Goeddel et al. |
| 5,785,054 A | 7/1998 | Kelly |
| 5,786,168 A | 7/1998 | Ishizaka et al. |
| 5,945,096 A | 8/1999 | Ishizaka et al. |
| 6,030,615 A | 2/2000 | Bucala et al. |
| 6,080,407 A | 6/2000 | Bucala et al. |
| 6,117,837 A | 9/2000 | Tracey et al. |
| 6,228,359 B1 | 5/2001 | Horwitz |
| 6,297,253 B1 | 10/2001 | Bukrinsky et al. |
| 6,395,276 B1 | 5/2002 | Rybak et al. |
| 6,492,428 B1 | 12/2002 | Al-Abed et al. |
| 6,599,938 B1 | 7/2003 | Al-Abed et al. |
| 6,645,493 B1 | 11/2003 | Bucala et al. |
| 6,774,227 B1 | 8/2004 | Bucala et al. |
| 6,998,238 B2 | 2/2006 | Bucala et al. |
| 7,514,225 B2 | 4/2009 | Gaeta et al. |
| 7,517,523 B2 | 4/2009 | Bucala et al. |
| 8,617,822 B2 | 12/2013 | Bucala et al. |
| 2003/0099653 A1 | 5/2003 | Bucala et al. |
| 2003/0212020 A1 | 11/2003 | Murray et al. |
| 2003/0235584 A1 | 12/2003 | Kloetzer et al. |
| 2004/0156848 A1 | 8/2004 | Bucala et al. |
| 2011/0158905 A1 | 6/2011 | Goldenberg et al. |

FOREIGN PATENT DOCUMENTS

| | | |
|---|---|---|
| CA | 2205680 | 11/1998 |
| CN | 1869207 A | 11/2006 |
| EP | 0 162 812 B1 | 9/1993 |
| JP | 09-077799 A | 3/1997 |
| RU | 2236251 C2 | 9/2004 |
| WO | WO 90/11301 A1 | 10/1990 |

(Continued)

OTHER PUBLICATIONS

Pro-Clin 300 Preservative, Sigma-Aldrich publication, 2009, www.safcsupplysolutions.com/proclin.*
Kerschbaumer et al., Journal of Biological Chemistry, 287(1):7446-7455, Mar. 2012.*
Baugh, J.A. et al., "Macrophage migration inhibitory factor," *Crit Care Med*, 2002, vol. 30, No. 1 (Suppl.), pp. S27-S35.
Bloom, B.R. et al., "Mechanism of a Reaction in Vitro Associated With Delayed-Type Hypersensitivity," *Science*, Jul. 1, 1966, vol. 153, pp. 80-82.

(Continued)

*Primary Examiner* — Marianne P Allen
(74) *Attorney, Agent, or Firm* — Morgan, Lewis & Bockius LLP

(57) ABSTRACT

The present invention pertains to the recognition that a specific oxMIF form of MIF is useful as a diagnostic marker in (MIF-related) diseases, in particular for example monitoring of disease progression. The present invention also pertains to the respective use of a diagnostic kit and a respective diagnostic assay and pertains to advantageous respective antibodies.

11 Claims, 21 Drawing Sheets

(56) References Cited

FOREIGN PATENT DOCUMENTS

| WO | WO 91/07418 A1 | 5/1991 |
|---|---|---|
| WO | WO 94/26307 A1 | 11/1994 |
| WO | WO 95/31468 A1 | 11/1995 |
| WO | WO 96/09389 A2 | 3/1996 |
| WO | WO 96/15242 A2 | 5/1996 |
| WO | WO 97/25344 A1 | 7/1997 |
| WO | WO 97/29635 A1 | 8/1997 |
| WO | WO 98/17314 A1 | 4/1998 |
| WO | WO 98/37178 A1 | 8/1998 |
| WO | WO 01/32606 A1 | 5/2001 |
| WO | WO 01/64749 A2 | 9/2001 |
| WO | WO 03/060468 A2 | 7/2003 |
| WO | WO 2005/020919 A2 | 3/2005 |
| WO | WO 2007/075270 A2 | 7/2007 |
| WO | WO 2007/134538 A1 | 11/2007 |
| WO | WO 2009/086920 A1 | 7/2009 |
| WO | WO 2011/090492 A1 | 7/2011 |
| WO | WO 2013/050453 A1 | 4/2013 |
| WO | WO 2013/050457 A1 | 4/2013 |

OTHER PUBLICATIONS

Calandra, T. et al., "MIF as a glucocorticoid-induced modulator of cytokine production," Nature, Sep. 7, 1995, vol. 377, pp. 68-71.

Calandra, T. et al., Macrophage Migration Inhibitory Factor: A Counter-Regulator of Glucocorticoid Action and Critical Mediator of Septic Shock,: Journal of Inflammation, 1996, vol. 47, pp. 39-51.

David, J.R., "Delayed Hypersensitivity In Vitro: Its Mediation by Cell-Free Substances Formed by Lymphoid Cell-Antigen Interaction," Pathology, 1966, vol. 56, pp. 72-77.

Galat, A. et al., "A diversified family of 12-kDa proteins with a high amino acid sequence similarity to macrophage migration-inhibitory actor (MIF)," Eur. J. Biochem., 1994, vol. 224, pp. 417-421.

Kawaguchi, T. et al., "A Monoclonal Antibody Against Migration Inhibitory Factor (MIF) Obtained by Immunization With MIF From the Human Lymphoblast Cell Line Mo," Journal of Leukocyte Biology, 1986, vol. 39, pp. 223-232.

Lue, H. et al., "Macrophage migration inhibitory factor (MIF) promotes cell survival by activation of the Akt pathway and role for CSN5/JAB1 in the control of autocrine MID activity," Oncogene, 2007, vol. 26, pp. 5046-5059.

Mitchell, R.A. et al., "Mechanisms and effectors of MIF-dependent promotion of tumourigenesis," Cellular Signalling, 2004, vol. 16, pp. 13-19.

Nishihira, J., "Macrophage Migration Inhibitory Factor (MIF): Its Essential Role in the Immune System and Cell Growth," Journal of Interferon and Cytokine Research, 2000, vol. 20, pp. 751-762.

Shimizu, T. et al., "Identification of macrophage migration inhibitory factor (MIF) in human skin and its immunohistochemical localization," FEBS Letters, 1996, vol. 381, pp. 199-202.

Sun, H-W. et al., "Crystal structure at 2.6-Å resolution of human macrophage migration inhibitory factor," Proc. Natl. Acad. Sci. USA, May 1996, vol. 93, pp. 5191-5196.

Watarai, H. et al., "Posttranslational modification of the glycosylation inhibiting factor (GIF) gene product generates bioactive GIF," PNAS, Nov. 21, 2000, vol. 97, No. 24, pp. 13251-13256.

Weiser, W.Y. et al., "Generation of Human Hybridomas Producing Migration Inhibitory Factor (MIF) and of Murine Hybridomas Secreting Monoclonal Antibodies to Human MIF," Cellular Immunology, 1985, vol. 90, pp. 167-178.

Weiser, W.Y. et al., "Molecular cloning of a cDNA encoding a human macrophage migration inhibitory factor," Proc. Natl. Acad. Sci. USA, Oct. 1989, vol. 86, pp. 7522-7526.

"Raji" cell line database from invitrogen, <www.invitrogen.com/site/us/en/home/support/Cell-Lines-Results/Cell-Lines-Detail.27.html>; downloaded May 19, 2012, 1 page.

"Raji" datasheet from ATCC, <www.atcc.org/attachments/17457.pdf>; downloaded May 19, 2012, 3 pages.

Abe, R. et al., "Regulation of the CTL Response by Macrophage Migration Inhibitory Factor," The Journal of Immunology, 2001, vol. 166, pp. 747-753.

Alam, J. et al., "Reporter Genes: Application to the Study of Mammalian Gene Transcription,"Analytical Biochemistry, 1990, vol. 188, pp. 245-254.

Amano, T. et al., "Blockade of macrophage migration inhibitory factor (MIF) prevents the antigen-induced response in a murine model of allergic airway inflammation," Inflamm. Res., 207, 56:24-31.

Angal, S. et al., "A Single Amino Acid Substitution Abolishes the Heterogeneity of Chimeric Mouse/Human (IgG4) Antibody," Molecular Immunology, 1993, vol. 30, No. 1, pp. 105-108.

Bacher, et al., Proc. Natl. Acad. Sci. USA, vol. 93, pp. 7849-7854, 1996.

Baerwald, C.G.O., et al., "Corticotropin Releasing Hormone (CRH) Promoter Polymorphisms in Various Ethnic Group of Patients with Rheumatoid Arthritis", Z Rheumatol., 59, 29-34 (2000).

Barton et al., Genes and Immunity, 2003, vol. 4, pp. 487-491.

Baugh, et al., "A Functional Promoter Polymorphism in the Macrophage Migration Inhibitory Factor (MIF) Gene Associated with Disease Severity in Rheumatoid Arthritis", Genes and Immunity, vol. 3, No. 3, May 2002.

BD Pharmingen technical data sheet for CD74 for purified mouse anti-human CD74 monoclonal antibody (clone M-B741), 2007, 2 pages.

Benigni, F. et al., "The Proinflammatory Mediator Macrophage Migration Inhibitory Factor Induces Glucose Catabolism in Muscle," Journal of Clin. Invest., 2000, vol. 106, No. 10, pp. 1291-1300.

Bernhagen et al. MIF is a noncognate ligand of CXC chemokine receptors for inflammatory and atherogenic cell recruitment. Nat Med 13(5): 587-596, 2007.

Bernhagen et al., "The emerging role of MIF in septic shock and infection," Biotherapy, 8: 123-127 (1995).

Bernhagen, et al., "MIF is a Pituitary-Derived Cytokine that Potentiates Lethal Endotoxaemia", Nature, vol. 365, pp. 756-759, 1993.

Borghesi et al., "Autologous anti-idiotypic antibody response is regulated by the level of circulating complementary idiotype," Immunology, Blackwell Science Ltd., p. 172-177, (1996).

Bucala, R., "MIF Rediscovered: Cytokine, Pituitary Hormone, and Glucocorticoid-Induced Regulator of the Immune Response", FASEB Journal, 10, 1607-1612 (1996).

Bucala, R., "MIF Rediscovered: Pituitary Hormone, and Glucocorticoid-Induced Regulator of Cytokine Production," Cytokine & Growth Factor Reviews, vol. 7, No. 1, pp. 19-24 (1996).

Buck et al., Biotechniques, 1999, vol. 27, pp. 528-536.

Burmeister, G. et al., "Generation and Characterization of a Monoclonal Antibody (1C5) to Human Inhibitory Factor (MIF)," Immunobiol., 1986, vol. 171, pp. 461-474.

Calandra et al. "The Macrophage Is an Important and Previously Unrecognized Source of Macrophage Migration Inhibitory Factor," J. Exp. Med, The Rockefeller University Press, vol. 179: 1895-1902, Jun. 1994.

Calandra, et al., Purification and Characterization of the cytokine macrophage migration inhibitory facto (MIF); abstract A1417.

Calandra, T., et al., "Protection From Septic Shock by Neutralization of Macrophage Migration Inhibitory Factor", Nature Medicine, vol. 6, No. 2, 164-170 (2000).

Calandra, T. et al., "MIF, A Previously Unrecognized Macrophage Cytokine, Induces 16. Macrophages to Secrete TNF-alpha and Overcomes Dexamethasone-Suppression of TNF Secretion," Clinical Research, 1994, vol. 42, No. 2, p. 138A.

Calandra, et al, "Macrophage Migration Inhibitory Factor: A Regulator of Innate Immunity,"Nature Reviews, 2003, vol. 3, pp. 791-800.

Chen, Z. et al.; "Evidence for a Role of Macrophage Migration Inhibitory Factor in Vascular Disease"; 2004, Arteriosclerosis, Thrombosis, and Vascular Biology, vol. 24, No. 4, pp. 709-714.

Chesney, J. et al., "An Essential Role for Macrophage Migration Inhibitory Factor (MIF) in Angiogenesis and the Growth of a Murine Lymphoma," Molecular Medicine, 1999, vol. 5, pp. 181-191.

(56) References Cited

OTHER PUBLICATIONS

Chikanza, I.C. et al., "Defective Hypothalamic Response to Immune and Inflammatory Stimuli in Patients with Rheumatoid Arthritis," *Arthritis and Rheumatism*, 1992, vol. 35, No. 11, pp. 1281-1288.
Cohen, L.E. et al., "Role of Pit-1 in the Gene Expression of Growth Hormone, Prolactin, and Thyrotropin," *Growth and Growth Disorders*, 1996, vol. 25, No. 3, pp. 523-540.
Colman Research in Immunology 145:33-36, 1984.
Cvetkovic et al., 2006, Neutralization of macrophage migration inhibitory factor—novel approach for the treatment of immunoinflammatory disorders, International Immunopharmacology, 6: 1527-1534.
Das, U.N., "Critical advances in septicemia and septic shock," *Grit Care*, 2000, vol. 4, pp. 290-296.
Donn, et al., "A Novel 5'-Flanking Region Polymorphism of Macrophage Migration Inhibitory Factor Is Associated with Systemic-Onset Juvenile Idiopathic Arthritis", Arthritis & Rheumatism, vol. 44, No. 8, pp. 1782-1785, Aug. 2001.
Donnelly, S.C. et al., "Macrophage Migration Inhibitory Factor and Acute Lung Injury," Chest, Jul. 1999, vol. 116, p. 111S.
Doria, G. et al., "Age-Dependent Variations of Antibody Avidity," Immunology, 35:601-611, 1978.
Duan, L. et al., "Preparation of peptides library and selection of B cell epitopes of Schistosoma japonicum calpain," Chin J Microbio Immuno, Jul. 2002, vol. 22, No. 4, pp. 411-414. (Translation of Abstract).
Elgert, KD., Immunology: Understanding the Immune System, 1996, A. John Wiley & Sons, Inc., pp. 86-89.
Epstein et al., "Characteristics and mode of growth of a tissue culture strain (EB1) of human lymphoblasts from Burkitt's lymphoma," J Natl Cancer Institute, 34(2): 231-240 (1965).
Fan, H. et al., "Macrophage Migration Inhibitory Factor and CD74 Regulate Macrophage Chemotactic Responses via MAPK and Rho GTPase," *The Journal of Immunology*, 2011, vol. 186, pp. 4915-4924.
Feldmann, M. et al., "Anti-TNF-alpha Therapy of Rheumatoid Arthritis: What Have We Learned?" Annu. Rev. Immunol., 2001, vol. 19, pp. 163-196.
Francis, S.E. et al., "Interleukin-1 Receptor Antagonist Gene Polymorphism and Coronary Artery Disease," Circulation, 1999, vol. 99, pp. 861-866.
Geczy, C.L. et al., "Production and Characterization of Antisera Against Human Macrophage Migration Inhibitory Factor (MIF)," Molecular Immunology, 1980, vol. 17, pp. 539-553.
Goidl, E.A. et. al., "Studies on the Control of Antibody Synthesis. VII. Change in Affinity of Direct and Indirect Plaque-Forming Cells With Time After Immunization in the Mouse: Loss of High Affinity Plaques Later After Immunization," Immunology, 29:629-641, 1975.
Gregerson et al., Arthritis & Rheumatism, 2003, vol. 48, pp. 1171-1176.
Grieb, G. et al., "Macrophage migration inhibitory factor is a potential inducer of endothelial progenitor cell mobilization after flap operation," *Surgery*, Feb. 1, 2012, vol. 151, No. 2, pp. 268-277.
Hagemann, T. et al., "Macrophages Induce Invasiveness of Epithelial Cancer Cells via NF-κB and JNK," *The Journal of Immunology*, 2005, vol. 175, pp. 1197-1205.
Hegele, Arterioscler. Thromb. Vasc. Biol., 2002, vol. 22, pp. 1058-1061.
Hertlein et al, Milatuzumab immunoliposomes induce cell death in CLL by accumulation of CD74 on the surface of B Cells, Blood, 116(14):2554-2558, 2010.
Horton, et al., "Potent in vitro and in vivo activity of an Fc-engineered anti-CD19 monoclonal antibody against lymphoma and leukemia," Cancer Res, 68(19): 8049-8057 (2008).
Hudson, J.D. et al., "A Proinflammatory Cytokine Inhibits p53 Tumor Suppressor Activity," J. Exp. Med., 1999, vol. 190, No. 10, pp. 1375-1382.

Ishiguro, Y. et al., "Macrophage migration inhibitory factor has a proinflammatory activity via the p38 pathway in glucocorticoid-resistant ulcerative colitis," *Clinical Immunology*, 2006, 120:335-341.
Lantz, A. et al., "Studies on the Control of Antibody Synthesis. VIII. Selection for High Affinity Antibody Production in the Secondary Response," Immunology 29:301-306, 1975.
Leech, et al., "Macrophage Migration Inhibitory Factor in Rheumatoid Arthritis", Arthritis & Rheumatism, vol. 42, No. 8, Aug. 1999, pp. 1601-1608.
Leech, M. et al., "Regulation of Macrophage Migration Inhibitory Factor by Endogenous Glucocorticoids in Rat Adjuvant-Induced Arthritis," *Arthritis & Rheumatism*, 2000, vol. 43, No. 4, pp. 827-833.
Leng et al. MIF signal transduction initiated by binding to CD74. J Exp Med 197(11): 1467-1476, 2003.
Leung, Joseph C.K. et al.; "Anti-macrophage migration inhibitory factor reduces transforming growth factor-111 expression in experimental IgA nephropathy"; 2004, Nephrol Dial Transplant, vol. 19, pp. 1976-1985.
Lucentini, The Scientist, 2004, vol. 24, p. 20.
MacCallum, R.M. et al., "Antibody-antigen Interactions: Contact Analysis and Binding Site Topography," J Mol. Biol. 262:732-745, 1996.
Makita, H. et al., "Effect of Anti-Macrophage Migration Inhibitory Factor Antibody on Lipopolysaccharide-induced Pulmonary Neutrophil Accumulation," *Am J Respir Crit Care Med*, 1998, 158:573-579.
Magi, et al., "Charge heterogeneity of macrophage migration inhibitory factor (MIF) in human liver and breast tissue", Electrophoresis, 19:2010-2013 (1998).
Mao et al., "Milatuzumab-conjugated liposomes as targeted dexamethasone carriers for therapeutic delivery in CD74+ B-cell malignancies," Clin Cancer Res, 19(2): 347-356 (2013).
McGuire, W. et al., "Variation in the TNF-alpha Promoter Region Associated With Susceptibility to Cerebral Malaria," Nature, 1994, vol. 371, pp. 508-510.
Merchant, A. et al., "Predominant Influence of Environmental Determinants on the Persistence and Avidity Maturation of Antibody Response to Vaccines in Infants," JID, 193:1598-1605, 2006.
Meyer-Siegler, K., "Macrophage Migration Inhibitory Factor Increases MMP-2 Activity in DU-145 Prostate Cells", Cytokine, vol. 12, No. 7, 914-921 (2000).
Meyer-Siegler, Katherine L. et al. "Inhibition of macrophage migration inhibitory factor decreases proliferation and cytokine expression in bladder cancer cells"; 2004, BMC Cancer, vol. 4, No. 1, 12 pages.
Meyer-Siegler, Katherine L. et al.; "Intraluminal Antibodies to Macrophage Migration Inhibitory Factor Decrease Substance P Induced Inflammatory Changes in the Rat Bladder and Prostate"; 2004, The Journal of Urology, vol. 172, pp. 1504-1509.
Mikulowska, A. et al., "Macrophage Migration Inhibitory Factor is Involved in the Pathogenesis of Collagen Type II-Induced Arthritis in Mice," The Journal of Immunology,1997, vol. 158, pp. 5514-5517.
Mitchell, R.A. et al., "Macrophage Migration Inhibitory Factor (MIF) Sustains Macrophage Proinflammatory Function by Inhibiting p53: Regulatory Role in the Innate Immune Response," PNAS, 2002, vol. 99, No. 1, pp. 345-350.
Mitchell, R.A. et al., "Sustained Mitogen-activated Protein Kinase (MAPK) and Cytoplasmic Phospholipase A2 Activation by Macrophage Migration Inhibitory Factor (MIF)," The Journal of Biological Chemistry, 1999, vol. 274, No. 25, pp. 18100-18106.
Morand, E.F. et al., "Macrophage migration inhibitory factor in rheumatoid arthritis: clinical correlations," Rheumatology, 2002, 41 :558-562.
Mu, H. et al., "Tumor Necrosis Factor a Microsatellite Polymorphism is Associated With Rheumatoid Arthritis Severity Through an Interaction With the HLA-DRB1 Shared Epitope," Arthritis & Rheumatism, 1999, vol. 42, No. 3, pp. 438-442.
Naylor, L.H., "Reporter Gene Technology: The Future Looks Bright," Biochemical Pharmacology, 1999, vol. 58, pp. 749-757.

(56) References Cited

OTHER PUBLICATIONS

Neng Lai, K. et al., "Role for macrophage migration inhibitory factor in acute respiratory distress syndrome," *Journal of Pathology*, 2003, 199:496-508.
Ngo, J.T. et al., "Computational Complexity, Protein Structure Prediction, and the Levinthal Paradox," *The Protein Folding Problem and Tertiary Structure Predictors*, 1994, pp. 492-495.
Nikolic-Paterson, D.J. et al., "MIF Gene Promoter Activity in Mesangial Cells—Induction by PDGF," *Journal of the American Society of Nephrology (Programs and Abstracts Issue)*, Sep. 2000, vol. 11, p. 478A, Abstract No. A2521.
Nimer, et al., "Adjacent, Cooperative, Elements Form a Strong, Constitutive Enhancer in the Human Granulocyte-Macrophage Colony-Stimulating Factor Gene", Blood, vol. 87, No. 9, pp. 3694-3703, 1996.
Nimer, et al., "The Repeated Sequence (CATT(A/T) is Required for Granulocyte-Macrophage Colony-Stimulating Factor Promoter Activity", Molecular and Cellular Biology, vol. 10, No. 11, pp. 6084-6088, 1990.
Ogawa, Hideaki et al.; "An Antibody for Macrophage Migration Inhibitory Factor Suppresses Tumour Growth and Inhibits Tumour-Associated Angiogenesis"; 2000, Cytokine, vol. 12, No. 4, pp. 309-314.
Onodera, et al., "Macrophage Migration Inhiitory Factor Up-regulates Expression of Matrix Metalloproteinases in Synovial Fibroblasts of Rheumatoid Arthritis", the Journal of Biological Chemistry, vol. 275, No. 1, Jan. 7, 2000, pp. 444-450.
Onodera, S. et al., "High Expression of Macrophage Migration Inhibitory Factor in the Synovial Tissues of Rheumatoid Joints," *Cytokine*, 1999, vol. 11, No. 2, pp. 163-167.
Orme Infection and Immunity 61(1):338-342, 1993.
Paralkar, V. et al., "Cloning the Human Gene for Macrophage Migration Inhibitory Factor (MIF)," Genomics, 1994, vol. 19, pp. 48-51.
Paul, William, Fundamental Immunology, 3rd ed., 1993, 292-295.
Payne, et al., "Clinical Laboratory Applications of Monoclonal Antibodies," Clin. Microbio. Rev. vol. 1, No. 3, pp. 313-329, 1988.
Prusiner, S.B. et al., "Ablation of the prion protein (PrP) gene in mice prevents scrapie and facilities production of anti-PrP antibodies," PNAS 90:10608-10612, 1993.
Pulvertaft et al., "Cytology of Burkitt's tumour (African lymphoma)," The Lancet, 1 (7327): 238-240 (1964).
Roger, T., et al. MIF regulates innate immune responses through modulation of Toll-like receptor 4. Nature, vol. 414, 20127 Dec. 2001, 920-924.
Rondard, P. et al., "Conformational and Functional Properties of an Undecapeptide Epitope Fused with the C-Terminal End of the Maltose Binding Protein," Biochemistry 36:8954-8961, 1997.
Rudikoff, S. et al., "Single amino acid substitution altering antigen-binding specificity," PNAS 79:1979-1983, 1982.
Rupreht, Ruth Rebeka et al.; "Murine monoclonal antibodies directed against human recombinant Macrophage Migration Inhibitory Factor"; 2000, European Journal of Physiology, vol. 440, No. 5, pp. R78-R80.
Sampey, A.V. et al., "Regulation of Synoviocyte Phospholipase A2 Cyclooxygenase 2 by Macrophage Migration Inhibitory Factor," Arlhritis & Rheumatism, 2001, vol. 44, No. 6, pp. 1273-1280.
Santos, L. et al., "Role of macrophage migration inhibitory factor (MIF) in murine antigen-induced arthritis: interaction with glucocorticoids," *Clin Exp Immunol*, 2001, 123:309-314.
Sashinami, H. et al., "The role of macrophage migration inhibitory factor in lethal *Listeria monocytogenes* infection in mice," *Microbial Pathogenesis*, 2006, 41:111-118.
Satoskar, A.R., et al., "Migration-Inhibitory Factor Gene-Deficient Mice Are Susceptible to Cutaneous Leishmania major Infection", Infection and Immunity, vol. 69, No. 2, 906-911 (2001).
Seamon, K.B. et al., "Forskolin: A Unique Diterpene Activator of Cyclic Amp-Generating Systems," Journal of Cyclic Nucleotide Research, 1981, vol. 7, No. 4, pp. 201-224.
Stosic-Grujicic, S. et al., "MIF in autoimmunity and novel therapeutic approaches," *Autoimmunity Reviews*, 2009, 8:244-249.
Sumida, Yorihisa et al.; "Anti-Macrophage Migration Inhibitory Factor Antibody Suppresses Chronic Rejection of Heterotopically Transplanted Trachea in Rats"; 2006, Acta Med. vol. 51, pp. 51-56.
Tagaya, et al., "Biochemical characterization of murine glycosylation-inhibiting factor", Proc. Natl. Acad. Sci. USA, 88:9117-9121 (1991).
Tsuda, T. et al., "Separation of Nucleotides by High-Voltage Capillary Electrophoresis," Journal of Applied Biochemistry, 1983, vol. 5, pp. 330-336.
Van Krugten, M.V. et al., "Association of the TNF +489 Polymorphism With Susceptibility and Radiographic Damage in Rheumatoid Arthritis," Gene and Immunity, 1999, vol. 1, pp. 91-96.
Waeber, G. et al., "Transcriptional Activation of the Macrophage Migration-Inhibitory Factor Gene by the Corticotropin-Releasing Factor is Mediated by the Cyclic Adenosine 3',5'-Monophosphate Responsive Element-Binding Protein CREB in Pituitary Cells," Molecular Endocrinology, 1998, vol. 12, No. 5, pp. 698-705.
Weiser, W.Y. et al., "Recombinant human migration inhibitory factor has adjuvant activity," Proc. Natl. Acad. Sci. USA, Sep. 1992, vol. 89, pp. 8049-8052
Wells, J.A., "Additivity of Mutational Effects in Proteins," Biochemistry, Sep. 18, 1990, vol. 29, No. 37, pp. 8509-8517.
Willis, Monte S. et al.; "Macrophage migration inhibitory factor mediates late cardiac dysfunction after burn injury"; 2005, American Journal of Physiology: Heart and Circulatory Physiology, vol. 288, No. 2, pp. H795-H804.
Wraight, Christopher J. et al., "Human Major Histocompatibility Complex Class 11 Invariant Chain Is Expressed on the Cell Surface", The Journal of Biological Chemistry, vol. 265, No. 10, Apr. 5, 1990, pp. 5787-5792.
Yang, N. et al., "Reversal of Established Rat Crescentic Glomerulonephritis by Blockade of Macrophage Migration Inhibitory Factor (MIF): Potential Role of MIF in Regulating Glucocorticoid Production," Molecular Medicine, 1998, vol. 4, pp. 413-424.
Ye, et al., "Identification of a DNA Binding Site for the Nuclear Factor YY1 in the Human GM-CSP Core Promoter," Nucleic Acids Research, vol. 22, No. 25, 5672-5678 (1994).
Ye, J. et al., "Characterization of the Human Granulocyte-Macrophage Colony-Stimulating Factor Gene Promoter: an AP1 Complex and an Sp1-Related Complex Transactive the Promoter Activity That is Suppressed by a YY1 Complex," *Molecular and Cellular Biology*, 1996, vol. 16, No. 1, pp. 157-167.

\* cited by examiner

Plasma obtained from control mice (C) and E.coli challenged mice (E) were subjected to oxMIF (Figure 1A) and total MIF (Figure 1B) ELISAs.

Detection of oxMIF in the plasma of bacteriemic patients

A

B

Means of oxMIF in urine from patients with Systemic lupus nephritis (different stages of the disease)

DIABETIC RETINOPATHY oxMIF on the surface of PC-3 prostate cancer cell line

Absence of oxMIF on surface of leukocytes from healthy donors oxMIF on the surface of BxPC-3 pancreatic cancer cell line oxMIF on the surface of A2780 ovarian cancer cell line oxMIF on the surface of human lymphoma cell line 14A Total MIF 14B oxMIF 15A Total MIF 15B oxMIF 16A CSF total MIF 16B CSF oxMIF Figure 17
Figure 17A
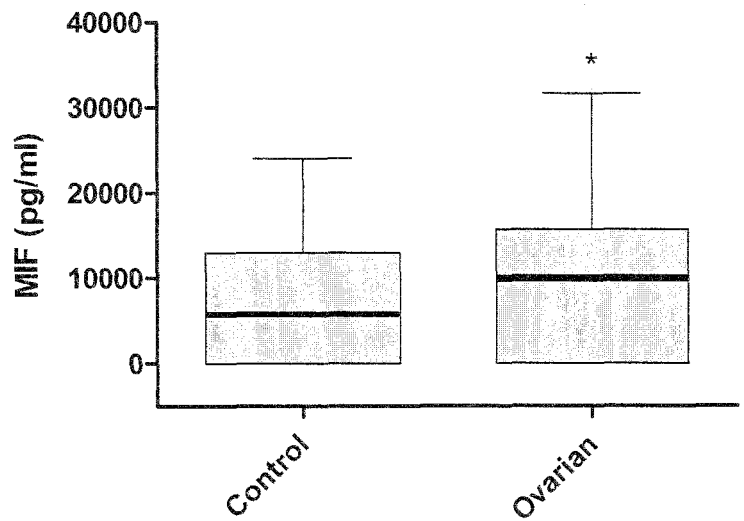
Figure 17B
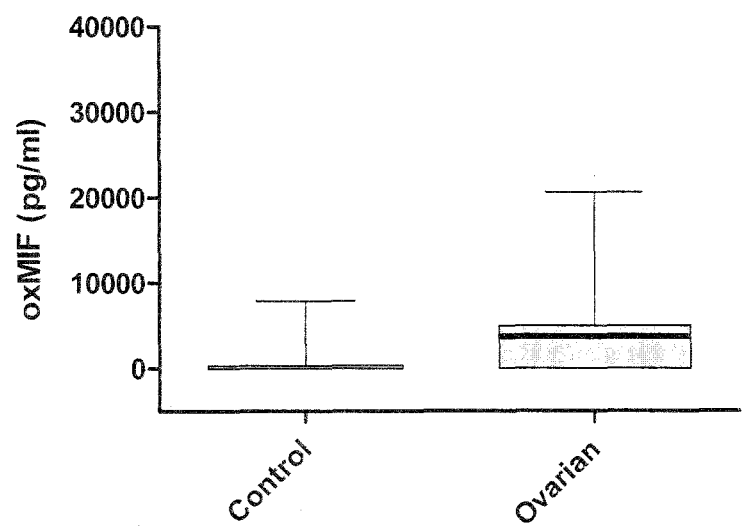

Figure 18
Figure 18A
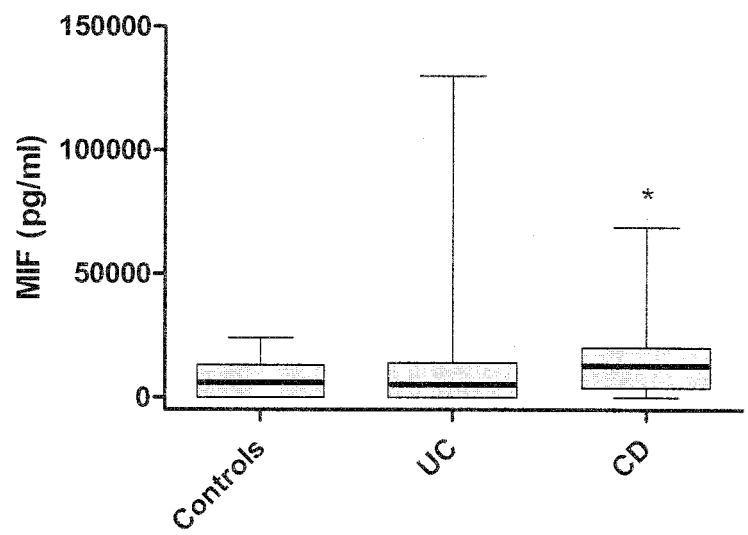
Figure 18B
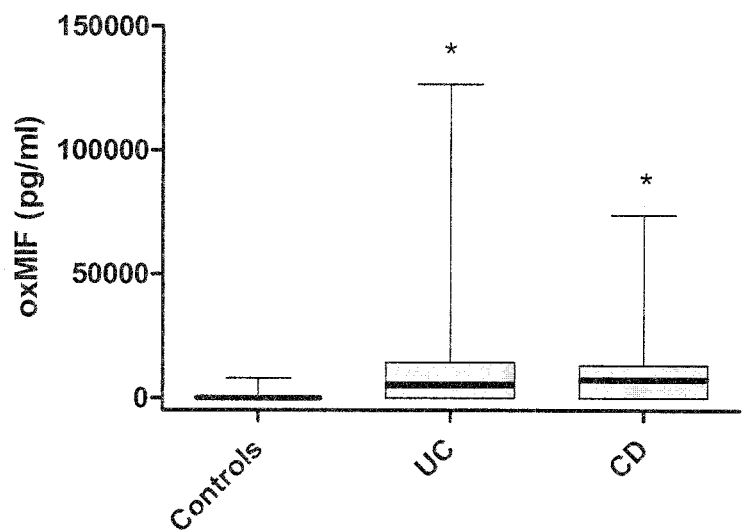

SEQUENCE LISTING

```
<160> NUMBER OF SEQ ID NOS: 14

<210> SEQ ID NO 1
<211> LENGTH: 214
<212> TYPE: PRT
<213> ORGANISM: Artificial Sequence
<220> FEATURE:
<223> OTHER INFORMATION: Light chain of RAB9

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 214
<212> TYPE: PRT
<213> ORGANISM: Artificial Sequence
<220> FEATURE:
<223> OTHER INFORMATION: Light chain of RAB4

<400> SEQUENCE: 2

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 214
<212> TYPE: PRT
<213> ORGANISM: Artificial Sequence
<220> FEATURE:
<223> OTHER INFORMATION: Light chain of RAB0

<400> SEQUENCE: 3

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 214
<212> TYPE: PRT
<213> ORGANISM: Artificial Sequence
<220> FEATURE:
<223> OTHER INFORMATION: Light chain of RAB2

<400> SEQUENCE: 4

Asp Ile Gln Met Thr Gln Ser Pro Val Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Thr Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 5
<211> LENGTH: 445
<212> TYPE: PRT
<213> ORGANISM: Artificial Sequence
<220> FEATURE:
<223> OTHER INFORMATION: Heavy chain of RAB9

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Ser Ile Gly Ser Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Gln Trp Leu Tyr Gly Met Asp Val Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285
```

```
Pro Arg Glu Glu Gln Phe Asn Ser Thr Tyr Arg Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 6
<211> LENGTH: 454
<212> TYPE: PRT
<213> ORGANISM: Artificial Sequence
<220> FEATURE:
<223> OTHER INFORMATION: Heavy chain of RAB4

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205
```

Thr Cys Asn Val Asp His Lys Pro Ser Asn Thr Lys Val Asp Lys Arg
            210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
            325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
            405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 7
<211> LENGTH: 454
<212> TYPE: PRT
<213> ORGANISM: Artificial Sequence
<220> FEATURE:
<223> OTHER INFORMATION: Heavy chain of RAB0

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ala Met Asp Trp Val Arg Gln Ala Pro Gly Lys Gly Leu Glu Trp Val
        35                  40                  45

Ser Gly Ile Tyr Pro Ser Gly Gly Arg Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Asn Val Ile Ala Val Ala Gly Thr Gly Tyr Tyr Tyr Tyr
            100                 105                 110

```
Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 8
<211> LENGTH: 454
<212> TYPE: PRT
<213> ORGANISM: Artificial Sequence
<220> FEATURE:
<223> OTHER INFORMATION: Heavy chain of RAB2

<400> SEQUENCE: 8

Glu Val Gln Leu Leu Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
            35                  40                  45

Ser Gly Ile Val Pro Ser Gly Gly Phe Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
 130                 135                 140

Thr Ser Glu Ser Thr Ala Ala Leu Gly Cys Leu Val Lys Asp Tyr Phe
 145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
            195                 200                 205

Thr Cys Asn Val Asp His Lys Pro Ser Asn Thr Lys Val Asp Lys Arg
 210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
            275                 280                 285

Val Glu Val His Asn Ala Lys Thr Lys Pro Arg Glu Glu Gln Phe Asn
 290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
            325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
 370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
            405                 410                 415

Leu Thr Val Asp Lys Ser Arg Trp Gln Glu Gly Asn Val Phe Ser Cys
            420                 425                 430

```
Ser Val Met His Glu Ala Leu His Asn His Tyr Thr Gln Lys Ser Leu
            435                 440                 445
Ser Leu Ser Leu Gly Lys
        450

<210> SEQ ID NO 9
<211> LENGTH: 457
<212> TYPE: PRT
<213> ORGANISM: Artificial Sequence
<220> FEATURE:
<223> OTHER INFORMATION: RAM0hc

<400> SEQUENCE: 9

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Trp Tyr
            20                  25                  30
Ala Met Asp Trp Val Arg Gln Ala Pro Gly Lys Gly Leu Glu Trp Val
        35                  40                  45
Ser Gly Ile Tyr Pro Ser Gly Gly Arg Thr Lys Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Asn Val Ile Ala Val Ala Gly Thr Gly Tyr Tyr Tyr Tyr
            100                 105                 110
Gly Met Asp Val Trp Gly Gln Gly Thr Thr Val Thr Val Ser Ser Ala
        115                 120                 125
Ser Thr Lys Gly Pro Ser Val Phe Pro Leu Ala Pro Ser Ser Lys Ser
    130                 135                 140
Thr Ser Gly Gly Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
            180                 185                 190
Ser Ser Val Val Thr Val Pro Ser Ser Ser Leu Gly Thr Gln Thr Tyr
        195                 200                 205
Ile Cys Asn Val Asn His Lys Pro Ser Asn Thr Lys Val Asp Lys Arg
    210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
            260                 265                 270
Val Val Asp Val Ser His Glu Asp Pro Glu Val Lys Phe Asn Trp Tyr
        275                 280                 285
Val Asp Gly Val Glu Val His Asn Ala Lys Thr Lys Pro Arg Glu Glu
    290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
```

```
Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 10
<211> LENGTH: 214
<212> TYPE: PRT
<213> ORGANISM: Artificial Sequence
<220> FEATURE:
<223> OTHER INFORMATION: RAM01c

<400> SEQUENCE: 10

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 448
```

```
<212> TYPE: PRT
<213> ORGANISM: Artificial Sequence
<220> FEATURE:
<223> OTHER INFORMATION: RAM9hc

<400> SEQUENCE: 11
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ile | Tyr |
| | | | 20 | | | | | 25 | | | | | 30 | | |
| Ser | Met | Asn | Trp | Val | Arg | Gln | Ala | Pro | Gly | Lys | Gly | Leu | Glu | Trp | Val |
| | | 35 | | | | | 40 | | | | | 45 | | | |
| Ser | Ser | Ile | Gly | Ser | Ser | Gly | Thr | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Gly | Ser | Gln | Trp | Leu | Tyr | Gly | Met | Asp | Val | Trp | Gly | Gln | Gly | Thr |
| | | | 100 | | | | | 105 | | | | | 110 | | |
| Thr | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| 130 | | | | | 135 | | | | | 140 | | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Lys | Arg | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | 275 | | | | | 280 | | | | | 285 | | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Glu | Glu | Met | Thr | Lys | Asn | Gln | Val | Ser | Leu | Thr | Cys |
| | | 355 | | | | | 360 | | | | | 365 | | | |
| Leu | Val | Lys | Gly | Phe | Tyr | Pro | Ser | Asp | Ile | Ala | Val | Glu | Trp | Glu | Ser |
| | 370 | | | | | 375 | | | | | 380 | | | | |

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 12
<211> LENGTH: 214
<212> TYPE: PRT
<213> ORGANISM: Artificial Sequence
<220> FEATURE:
<223> OTHER INFORMATION: RAM9lc

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 457
<212> TYPE: PRT
<213> ORGANISM: Artificial Sequence
<220> FEATURE:
<223> OTHER INFORMATION: RAM4hc

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

```
Ala Met Asp Trp Val Arg Gln Ala Pro Gly Lys Gly Leu Glu Trp Val
         35                  40                  45

Ser Gly Ile Val Pro Ser Gly Gly Phe Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Val Asn Val Ile Ala Val Ala Gly Thr Gly Tyr Tyr Tyr Tyr
                100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
                195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445
```

```
Lys Ser Leu Ser Leu Ser Pro Gly Lys
    450                 455

<210> SEQ ID NO 14
<211> LENGTH: 214
<212> TYPE: PRT
<213> ORGANISM: Artificial Sequence
<220> FEATURE:
<223> OTHER INFORMATION: RAM41c

<400> SEQUENCE: 14

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

OXMIF AS A DIAGNOSTIC MARKER

This application is a U.S. National Phase application of International Patent Application No. PCT/EP2012/069598, filed Oct. 4, 2012, which claims the benefit of U.S. Provisional Patent Application No. 61/545,042, filed Oct. 7, 2011, U.S. Provisional Patent Application No. 61/624,943, filed Apr. 16, 2012, and U.S. Provisional Patent Application No. 61/668,841, filed Jul. 6, 2012, all of which are hereby incorporated herein by reference in their entireties.

The present invention pertains to the recognition that a specific MIF form is useful as a diagnostic marker in MIF-related diseases, in particular for example for monitoring of disease progression, as a (secondary) marker of a (MIF related) disease condition, or as a tool assisting in treatment decisions, in particular in body fluids or on cells or cell surfaces. The present invention also pertains to the respective use of a diagnostic kit and a respective diagnostic assay.

BACKGROUND

Macrophage migration inhibitory factor (MIF) is a cytokine initially isolated based upon its ability to inhibit the in vitro random migration of peritoneal exudate cells from tuberculin hypersensitive guinea pigs (containing macrophages) (Bloom et al. Science 1966, 153, 80-2; David et al. PNAS 1966, 56, 72-7). Today, MIF is known as a critical upstream regulator of the innate and acquired immune response that exerts a pleiotropic spectrum of activities.

The human MIF cDNA was cloned in 1989 (Weiser et al., PNAS 1989, 86, 7522-6), and its genomic localization was mapped to chromosome 22. The product of the human MIF gene is a protein with 114 amino acids (after cleavage of the N-terminal methionine) and an apparent molecular mass of about 12.5 kDa. MIF has no significant sequence homology to any other protein. The protein crystallizes as a trimer of identical subunits. Each monomer contains two antiparallel alpha-helices that pack against a four-stranded beta-sheet. The monomer has additional two beta-strands that interact with the beta-sheets of adjacent subunits to form the interface between monomers. The three subunits are arranged to form a barrel containing a solvent-accessible channel that runs through the center of the protein along a molecular three-fold axis (Sun et al. PNAS 1996, 93, 5191-5196).

It was reported that MIF secretion from macrophages was induced at very low concentrations of glucocorticoids (Calandra et al. Nature 1995, 377, 68-71). However, MIF also counter-regulates the effects of glucocorticoids and stimulates the secretion of other cytokines such as tumor necrosis factor TNF-α and interleukin IL-1β (Baugh et al., Crit. Care Med 2002, 30, S27-35). MIF was also shown e.g. to exhibit pro-angiogenic, pro-proliferative and anti-apoptotic properties, thereby promoting tumor cell growth (Mitchell, R. A., Cellular Signalling, 2004. 16(1): p. 13-19; Lue, H. et al., Oncogene 2007. 26(35): p. 5046-59). It is also e.g. directly associated with the growth of lymphoma, melanoma, and colon cancer (Nishihira et al. J Interferon Cytokine Res. 2000, 20:751-62).

MIF is a mediator of many pathologic conditions and thus associated with a variety of diseases including inter alia inflammatory bowel disease (IBD), rheumatoid arthritis (RA), acute respiratory distress syndrome (ARDS), asthma, glomerulonephritis, IgA nephropathy, myocardial infarction (MI), sepsis and cancer, though not limited thereto.

Polyclonal and monoclonal anti-MIF antibodies have been developed against recombinant human MIF (Shimizu et al., FEBS Lett. 1996; 381, 199-202; Kawaguchi et al, Leukoc. Biol. 1986, 39, 223-232, and Weiser et al., Cell. Immunol. 1985, 90, 16778).

Anti-MIF antibodies have been suggested for therapeutic use. Calandra et al., (J. Inflamm. (1995); 47, 39-51) reportedly used anti-MIF antibodies to protect animals from experimentally induced gram-negative and gram-positive septic shock. Anti-MIF antibodies were suggested as a means of therapy to modulate cytokine production in septic shock and other inflammatory disease states.

U.S. Pat. No. 6,645,493 discloses monoclonal anti-MIF antibodies derived from hybridoma cells, which neutralize the biological activity of MIF. It could be shown in an animal model that these mouse-derived anti-MIF antibodies had a beneficial effect in the treatment of endotoxin induced shock.

US 200310235584 discloses methods of preparing high affinity antibodies to MIF in animals in which the MIF gene has been homozygously knocked-out.

Glycosylation-inhibiting factor (GIF) is a protein described by Galat et al. (Eur. J. Biochem, 1994, 224, 417-21). MIF and GIF are now recognized to be identical. Watarai et al. (PNAS 2000, 97, 13251-6) described polyclonal antibodies binding to different GIF epitopes to identify the biochemical nature of the posttranslational modification of GIF in Ts cells. Watarai et al, supra, reported that GIF occurs in different conformational isoforms in vitro. One type of isomer occurs by chemical modification of a single cysteine residue. The chemical modification leads to conformational changes within the GIF protein.

As has been shown over the past decades that MIF is a molecule which is involved in a multitude of different interactions, it might therefore be a suitable marker for disease states in MIF-related diseases. Although diagnostic markers and methods for several of those diseases which are MIF-related exist, it is usually advantageous to have more than one method or marker for the diagnosis of a given disease, and—even more importantly—to have a marker which is correlated with an actual disease state. MIF is a ubiquitous protein detectable in high amounts in the human body and therefore no clear connection between appearance of MIF and (MIF-related) diseases could be made in general. Therefore, there exists a need in the art for a suitable diagnostic marker to detect the onset and/or existence of (MIF-related) diseases in a subject; in particular, there is a need for a reliable marker which would allow monitoring of disease progression, determining a disease state and monitoring efficacy of a treatment in (MIF-related) diseases, in particular by using body fluids as samples or by using cells as samples.

DESCRIPTION OF THE INVENTION

The above objects have been solved by the present invention. In particular, the present inventors could show that oxMIF (i.e. oxidized MIF) can be detected after onset of (MIF-related) diseases, e.g. in body fluid samples, or on cells or cell surfaces and that oxMIF is correlated with a disease state and/or the disease progression. Based on the presently provided knowledge/techniques, oxMIF is not present in body fluid samples, like e.g. blood, serum and urine, from healthy donors or in cellular samples from healthy donors. OxMIF is increased under disease conditions. This increase is more pronounced (more specific) than for total MIF (see also the examples).

"is not present" in this context shall mean that oxMIF is not present in body fluids in amounts which are detectable with the ELISA-techniques as shown in Example 3.4 under the heading "Material and Methods", if carried out with the antibody RAB0, described below.

"Is not present" in the context of cellular samples, e.g. blood cells, means that in cellular samples application of the antibody RAB9 or RAB0 or RAB4 on the cells does not give a higher signal when compared to the staining with the control antibody "Control 1" in a flow cytometry experiment as described in example 3.9.

Therefore, oxMIF is suitable as a marker for these diseases, whereby the terminology "marker in the diagnosis of a (MIF related) disease" in the context of the present invention shall mean in particular the possibility for an evaluation whether or not MIF is a factor involved in this (MIF related) disease. In that regard oxMIF as marker supplies information about the disease state, its progression and serves as a marker to determine effectiveness of a given treatment; in addition, oxMIF detection in a sample, e.g. a body fluid sample or a cell sample, can serve as an indicator for a preferred anti-MIF therapy. The detection of oxMIF thus serves to improve known diagnostic techniques in a given disease or disorder. It assists the practitioner in his or her decision how to treat a given disease or disorder and helps to improve specificity of the diagnosis. oxMIF is thus a specific and suitable secondary marker. Its detection can thus serve as an adjunctive test in the management of patients afflicted with MIF related diseases. The disease in question is in a preferred embodiment a disease which is known or suspected to be MIF related (see the diseases mentioned in detail below) but can also be a disease which had so far not been suspected to be MIF related.

In a preferred embodiment, the detection of oxMIF presence in a sample would indicate to the practitioner that the subject, from whom (or which) the sample has been taken, might benefit from a therapy directed against MIF. Such a therapy could be selected from anti-MIF molecules, e.g. anti-(ox)MIF antibodies or small molecules which are directed against (ox) MIF.

Elevated MIF levels, i.e. levels of MIF in general are detected after the onset of various diseases, inter alia after the onset of cancer. However, MIF circulates also in healthy subjects, which makes a clear differentiation difficult. oxMIF, on the contrary, is not present in healthy subjects and therefore is a much stronger diagnostic marker for MIF-related diseases. As shown in the examples, oxMIF is increased in disease states and detectable in samples of patients, like e.g. blood, serum and urine.

The invention presented here is based—inter alia—on the finding that the Baxter antibodies RAB9, RAB4 and RAB0 specifically bind to oxMIF (and are incapable of binding to redMIF).

In earlier experiments carried out by the inventors, it could be shown that oxidative procedures like cystine-mediated oxidation, GSSG (ox. Glutathione)-mediated oxidation or incubation of MIF with Proclin300 or protein crosslinkers (e.g. BMOE) causes binding to the above mentioned antibodies.

The surprising conclusions reached by the present inventors are:
  Redox modulation (Cys/Glu-mediated mild oxidation) of recombinant MIF (human, murine, rat, CHO, monkey)) or treatment of recombinant MIF with Proclin300 or protein crosslinkers leads to the binding of Baxter's anti-MIF antibodies RAB9, RAB4 and RAB0
  Reduction of oxMIF leads to the loss of Ab binding
  Specificity for oxMIF-isoforms correlates with biological Ab efficacy (in vitro/in vivo).
  oxMIF levels can be correlated with a disease state.

Thus, the present invention is preferably defined as follows:

1. Use of oxMIF as a marker in the in vitro diagnosis of (MIF-related) diseases, wherein oxMIF is MIF which is differentially binding to antibody RAB9, RAB0 and/or RAB4.
2. The use of item 1 wherein said diagnosis of (MIF-related diseases) further involves the use of compounds differentially binding to the diagnostic marker, which is oxMIF, as defined in item 1.
3. The use according to item 2 wherein the compounds are antibodies, differentially binding to oxMIF.
4. The use according to item 3 wherein the antibodies bind to oxMIF, but do not bind to red MIF.
5. The use according to item 4 wherein the differential binding is a binding to oxMIF which occurs with a $K_D$ value of less than 100 nM, preferably less than 50 nM, even more preferred less than 100 nM and a non-binding to redMIF which is characterized by a $K_D$ of more than 400 nM.
6. The use according to any one or more of items 1 to 5, wherein the MIF-related diseases are selected from the group comprising: inflammatory diseases and neoplastic diseases (benign, pre-malignant and/or malignant).
7. The use according to item 6 wherein the MIF-related diseases are selected from the group, consisting of colon cancer, prostate cancer, bladder cancer, pancreas cancer, ovarian cancer, melanoma, lymphoma, hepatocellular carcinoma, asthma, ARDS, rheumatoid arthritis, sepsis, IgA nephropathy, glomerulonephritis, Lupus Nephritis (LN), hepatitis, pancreatitis (+/−acute lung injury), Crohn's disease, ulcerative colitis, gastric ulcer, Alzheimer's disease, multiple sclerosis, Guillain-Barre syndrome, cardiac dysfunction, angioplasty, atherosclerosis, myocarditis, type 1 diabetes, diabetic retinopathy, age-related macula degeneration (AND), atopic dermatitis, psoriasis, endometriosis, neuropathic pain and/or uveitis.
8. The use according to any one or more of items 2 to 7 wherein the antibodies are selected from the group consisting of oxMIF binders (like e.g. antibodies RAB9, RAB4 and/or RAB0)).
9. The use according to any one of items 1 to 8, wherein the diagnosis is the diagnosis of the existence of a (MIF-related disease), the diagnosis of progression of a (MIF-related disease), the diagnosis of the state of a disease, and/or the monitoring of effectiveness of a treatment.
10. The use according to any one of items 1 to 9, wherein the diagnosis is carried out on a body fluid sample of a subject.
11. The use according to any one of items 1 to 9, wherein the diagnosis is carried out on a cellular sample of a subject.
12. A diagnostic assay for in vitro diagnosis of (MIF-related) diseases by detection of oxMIF as defined in item 1 in a body fluid or a cellular sample of a subject, comprising a step of determining binding of a compound to oxMIF in said sample in vitro.
13. The diagnostic assay according to item 12 wherein the compound binding to oxMIF and the (MIF-related) diseases are as defined in any one or more of items 2 to 9.
14. The diagnostic assay according to item 12 or 13, wherein the assay is repeated once or several times during progression, remission and/or treatment of a (MIF-related) disease.
15. Use of a diagnostic kit in the assay of any one or more of items 12 to 14, wherein the diagnostic kit comprises a compound binding to oxMIF.

16. The use according to item 15 wherein the kit additionally comprises buffers, controls (e.g. recombinant (ox)MIF), polyclonal MIF antibody, and/or conjugated detection antibody.
17. Anti-MIF antibody, which is selected from the following group:
    a) a RAB4 antibody, characterized by a light chain sequence as deposited by way of plasmid deposition with deposit number DSM 25110 and a heavy chain sequence as deposited by way of plasmid deposition with deposit number DSM 25112,
    b) a RAB9 antibody, characterized by a light chain sequence as deposited by way of plasmid deposition with deposit number DSM 25111 and a heavy chain sequence as deposited by way of plasmid deposition with deposit number DSM 25113,
    c) a RAB0 antibody, characterized by a light chain sequence as deposited by way of plasmid deposition with deposit number DSM 25114 and a heavy chain sequence as deposited by way of plasmid deposition with deposit number DSM 25115,
    d) a RAM4 antibody, characterized by a light chain sequence as deposited by way of plasmid deposition with deposit number DSM 25861 and a heavy chain sequence as deposited by way of plasmid deposition with deposit number DSM 25862,
    e) a RAM9 antibody, characterized by a light chain sequence as deposited by way of plasmid deposition with deposit number DSM 25859 and a heavy chain sequence as deposited by way of plasmid deposition with deposit number DSM 25860, and/or
    f) a RAM0 antibody, characterized by a light chain sequence as deposited by way of plasmid deposition with deposit number DSM 25863 and a heavy chain sequence as deposited by way of plasmid deposition with deposit number DSM 25864.
18. Anti-MIF antibody, which is selected from the following group:
    a) a RAB4 antibody, which is characterized by a light chain amino acid sequence of SEQ ID NO: 2 and a heavy chain amino acid sequence of SEQ ID NO:6,
    b) a RAB9 antibody, which is characterized by a light chain amino acid sequence of SEQ ID NO: 1 and a heavy chain amino acid sequence of SEQ ID NO:5,
    c) a RAB0 antibody, which is characterized by a light chain amino acid sequence of SEQ ID NO: 3 and a heavy chain amino acid sequence of SEQ ID NO:7,
    d) a RAB2 antibody, which is characterized by a light chain amino acid sequence of SEQ ID NO: 4 and a heavy chain amino acid sequence of SEQ ID NO:8,
    e) a RAM4 antibody, which is characterized by a light chain amino acid sequence of SEQ ID NO: 14 and a heavy chain amino acid sequence of SEQ ID NO:13,
    f) a RAM9 antibody, which is characterized by a light chain amino acid sequence of SEQ ID NO: 12 and a heavy chain amino acid sequence of SEQ ID NO: 11, and/or
    g) a RAM0 antibody, which is characterized by a light chain amino acid sequence of SEQ ID NO: 10 and a heavy chain amino acid sequence of SEQ ID NO:9
    h) or functional equivalents thereof which are characterized by binding to the same epitope as any one of the antibodies a) to g) above.
19. Use of any one of the above antibodies, in particular as defined in items 17 or 18, in the diagnosis of a (MIF-related) disease.

All above mentioned items as well as the claims annexed hereto pertain equally to the following preferred antibodies:
RAM9
RAM4
RAM0.
These antibodies have the same specificities as the antibodies mentioned in the above list of items (see also below); similar results can be achieved with these antibodies.
In particular, with the present invention, preferred inventive antibodies, which are particularly suitable and advantageous, e.g. as diagnostic markers, are provided.

These above mentioned antibodies are characterized and supported by both their sequences as well as by deposits as plasmids in *E. coli*(strain TG1), comprising either the light or the heavy chain of each of the above mentioned antibodies RAB0, RAB4 and RAB9, respectively as well as of RAM0, RAM4 and RAM9.

The plasmids are characterized by their DSM number which is the official number as obtained upon deposit under the Budapest Treaty with the German Collection of Microorganisms and Cell Cultures (DSMZ), Mascheroder Weg 1b, Braunschweig, Germany. The plasmids were deposited in *E. coli* strains, respectively.

The plasmid with the DSM 25110 number comprises the light chain sequence of the anti-MIF antibody RAB4.

Accession number DSM 25110 was deposited with the DSMZ-DEUTSCHE SAMMLUNG VON MIKROORGANISMEN UND ZELLKULTUREN GmbH located in Braunschweig, Germany on Aug. 31, 2011.

The plasmid with the DSM 25112 number comprises the heavy chain (IgG4) sequence of the anti-MIF antibody RAB4.

Accession number DSM 25112 was deposited with the DSMZ-DEUTSCHE SAMMLUNG VON MIKROORGANISMEN UND ZELLKULTUREN GmbH located in Braunschweig, Germany on Aug. 31, 2011.

The co-expression of plasmids DSM 25110 and DSM 25112 in a suitable host cell results in the production of preferred anti-MIF antibody RAB4.

The plasmid with the DSM 25111 number comprises the light chain sequence of the anti-MIF antibody RAB9.

Accession number DSM 25111 was deposited with the DSMZ-DEUTSCHE SAMMLUNG VON MIKROORGANISMEN UND ZELLKULTUREN GmbH located in Braunschweig, Germany on Aug. 31, 2011.

The plasmid with the DSM 25113 number comprises the heavy chain (IgG4) sequence of the anti-MIF antibody RAB9.

Accession number DSM 25113 was deposited with the DSMZ-DEUTSCHE SAMMLUNG VON MIKROORGANISMEN UND ZELLKULTUREN GmbH located in Braunschweig, Germany on Aug. 31, 2011.

The co-expression of plasmids DSM 25111 and DSM 25113 in a suitable host cell results in the production of preferred anti-MIF antibody RAB9.

The plasmid with the DSM 25114 number comprises the light chain sequence of the anti-MIF antibody RAB0.

Accession number DSM 25114 was deposited with the DSMZ-DEUTSCHE SAMMLUNG VON MIKROORGANISMEN UND ZELLKULTUREN GmbH located in Braunschweig, Germany on Aug. 31, 2011.

The plasmid with the DSM 25115 number comprises the heavy chain (IgG4) sequence of the anti-MIF antibody RAB0.

Accession number DSM 25115 was deposited with the DSMZ-DEUTSCHE SAMMLUNG VON MIKROOR- GANISMEN UND ZELLKULTUREN GmbH located in Braunschweig, Germany on Aug. 31, 2011.

The co-expression of plasmids DSM 25114 and DSM 25115 in a suitable host cell results in the production of preferred anti-MIF antibody RAB0.

Also deposited are antibodies RAM0, RAM9 and RAM4; all have been deposited with the DSZM, Braunschweig, Germany on Apr. 12, 2012 according to the Budapest Treaty, with the following designations:

RAM9—heavy chain: E. coli GA.662-01.pRAM9hc—DSM 25860.
RAM4—light chain: E. coli GA.906-04.pRAM4lc—DSM 25861.
RAM9—light chain: E. coli GA.661-01.pRAM9lc—DSM 25859.
RAM4—heavy chain: E. coli GA.657-02.pRAM4hc—DSM 25862.
RAM0—light chain: E. coli GA.906-01.pRAM0lc—DSM 25863.
RAM0—heavy chain: E. coli GA.784-01.pRAM0hc—DSM 25864.

Accession number DSM 25860 was deposited with the DSMZ-DEUTSCHE SAMMLUNG VON MIKROORGANISMEN UND ZELLKULTUREN GmbH located in Braunschweig, Germany on Apr. 12, 2012.

Accession number DSM 25861 was deposited with the DSMZ-DEUTSCHE SAMMLUNG VON MIKROORGANISMEN UND ZELLKULTUREN GmbH located in Braunschweig, Germany on Apr. 12, 2012.

Accession number DSM 25859 was deposited with the DSMZ-DEUTSCHE SAMMLUNG VON MIKROORGANISMEN UND ZELLKULTUREN GmbH located in Braunschweig, Germany on Apr. 12, 2012.

Accession number DSM 25862 was deposited with the DSMZ-DEUTSCHE SAMMLUNG VON MIKROORGANISMEN UND ZELLKULTUREN GmbH located in Braunschweig, Germany on Apr. 12, 2012.

Accession number DSM 25863 was deposited with the DSMZ-DEUTSCHE SAMMLUNG VON MIKROORGANISMEN UND ZELLKULTUREN GmbH located in Braunschweig, Germany on Apr. 12, 2012.

Accession number DSM 25864 was deposited with the DSMZ-DEUTSCHE SAMMLUNG VON MIKROORGANISMEN UND ZELLKULTUREN GmbH located in Braunschweig, Germany on Apr. 12, 2012.

The invention thus also encompasses a diagnostic assay comprising an anti-oxMIF antibody or antigen-binding fragment thereof whereby these antibodies or antigen-binding fragments thereof have a differential binding, i.e. bind to oxMIF but do not bind to redMIF for use in diagnostic methods. Based on the current knowledge/techniques, oxMIF cannot be detected in samples from healthy donors. In one embodiment the above anti-oxMIF antibody or antigen-binding portion thereof can be used to detect human oxMIF in a biological sample from a human subject.

A biological sample in the context of this application is preferably a body fluid sample of the subject on which/whom the diagnosis shall be performed. A body fluid sample is any sample of a body fluid as known to a person skilled in the art. Exemplary, but not limiting, such a sample can be blood, plasma, serum, saliva, urine, nasal fluid, ascites, ocular fluid, amniotic fluid, aqueous humour, vitreous humour, tear fluid, Cowper's fluid, semen, interstitial fluid, lymph, breast milk, mucus (incl. snot and phlegm), pleural fluid, pus, menses, vaginal lubrication, sebum, cerebrospinal fluid and synovial fluid. Further biological samples in the context of this application can be lavages (washing outs) of a (hollow) body organ (e.g. bronchoalveolar lavage, stomach lavage and bowel lavage).

A biological sample in the context of this application in an alternative embodiment, is a cell sample, most preferably a cell sample from the circulation or the diseased tissue, more preferably as a single cell suspension sample, of the subject on which the diagnosis shall be performed.

In particular, the above diagnostic assay can be used to determine whether (ox)MIF is involved in a given disease.

The present invention thus also pertains to a method for evaluating the progression of a disease; in the present context the term "state of a disease" is to be understood as synonymous with the term "severity of a disease" and refers to the seriousness, degree or state (i.e. stage) of a disease or condition. For example, a disease may be characterised as mild, moderate or severe. The determination or assessment of the degree of severity or the degree, i.e. state of the disease is well known to a person skilled in the art. The actual method which will be carried out for this assessment of course depends on the disease or condition in question. For example, the state of a disease may be determined by comparing the likelihood or length of survival of a subject having a disease with the likelihood or length of survival in other subjects having the same disease.

In other embodiments the state of the disease may be determined by comparing the symptoms of a disease in a subject having a disease with the symptoms in other subjects having the same disease. In yet another embodiment the state of the disease and its progression is reflected by the change of symptoms within one and the same patient over a period of time.

In a further preferred aspect, the present invention can also be directed to a method of selecting a subject as being eligible for a treatment with an anti-(ox)MIF compound, wherein the subject has a (MIF-related) disease, or is at risk of developing a (MIF-related) disease, comprising detecting the existence and/or level and/or change of level of oxMIF in said subject. A subject having an elevated level of oxMIF can be selected for a prophylactic or therapeutic treatment with an anti (ox)MIF compound as defined above.

The term "prophylactic" or "therapeutic" treatment is art-recognized and refers to administration of a drug to a patient. If it is administered prior to clinical manifestation of the unwanted condition (e.g. disease or other unwanted state of the host, e.g. a human or an animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects thereof).

As used herein an anti-(ox)MIF compound refers to any agent that attenuates, inhibits, opposes, counteracts, or decreases the biological activity of (ox)MIF. An anti(ox)MIF compound may be an agent that inhibits or neutralizes (ox)MIF activity, for example an antibody, particularly preferred, the antibodies as described herein, even more preferred the antibodies RAB9, RAB4 and/or RAB0.

The diagnostic assay can be used to determine an oxMIF presence or level in e.g. body fluid samples or cellular samples of patients. The presence or absence of oxMIF is suitable to distinguish, if the disease if MIF relevant or to decide of oxMIF treatment is reasonable. OxMIF levels indicate disease progression or treatment efficacy.

The invention further relates to kits comprising an anti-oxMIF antibody or an antigen-binding portion thereof according to the invention. A kit may include in addition to the antibody, further diagnostic or therapeutic agents and

DETAILED DESCRIPTION OF THE INVENTION

The invention is further described in the figures as enclosed.

Plasma obtained from control mice (C) and *E. coli* challenged mice (E) were subjected to oxMIF (FIG. 1A) and total MIF (FIG. 1B) ELISAs.

Figure 2:
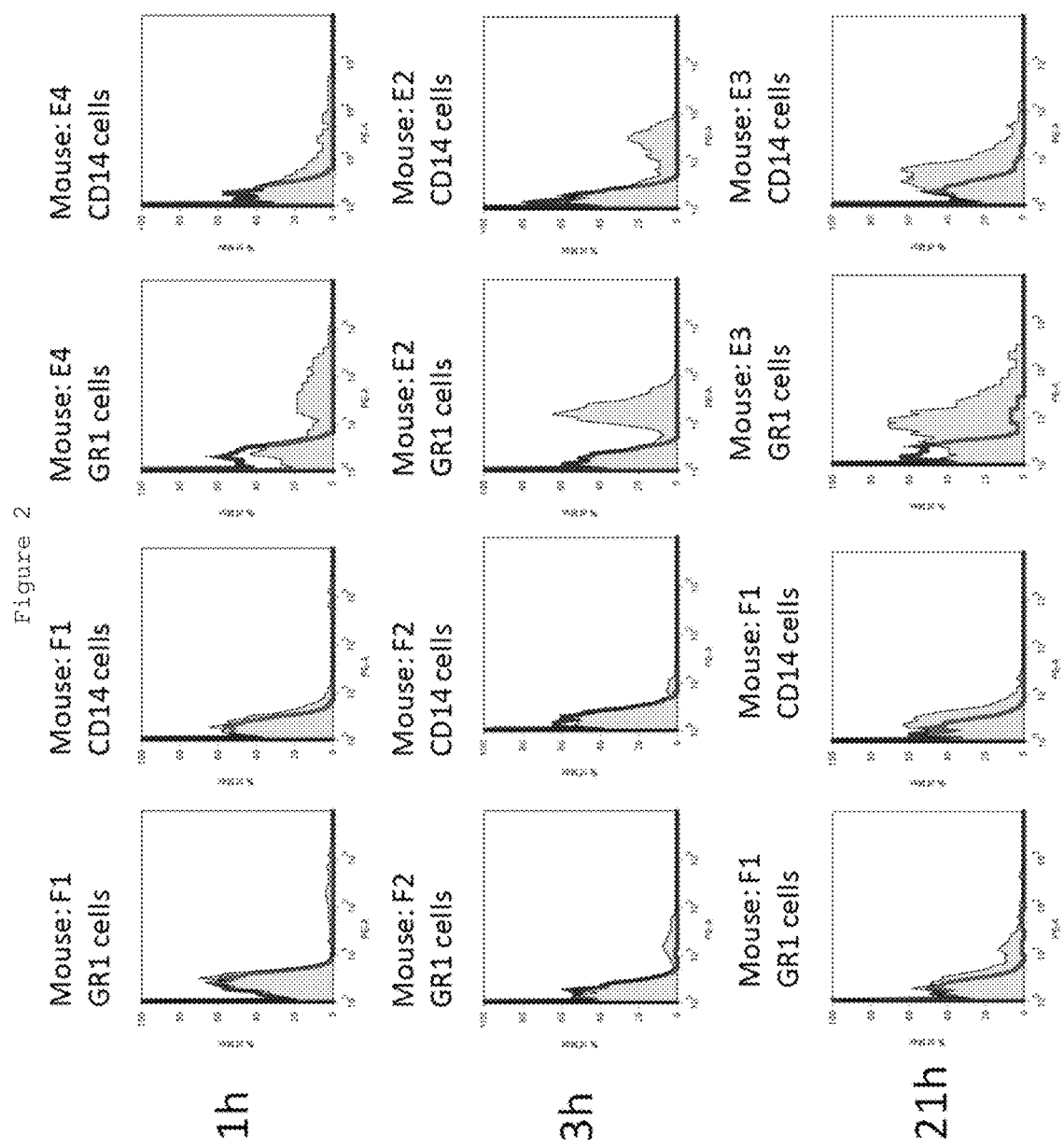

FIG. 2: oxMIF detection on the surface of granulocytes and monocytes from *E. coli* challenged mice Blood samples obtained at different time points from control (F) or *E. coli* challenged mice (E) were stained with specific cell markers to discriminate the leukocyte populations, and human anti-MIF monoclonal antibody RAB9 or human control IgG1 detected by an RPE (R-phycoerythrin, a chromogenic marker)-labeled polyclonal anti-human IgG. Histograms are showing overlays of the control antibody (thick black line) with the RAB9 specific staining (grey profile) in the granulocyte population (GR1) or the monocyte population (CD14).

Figure 3:
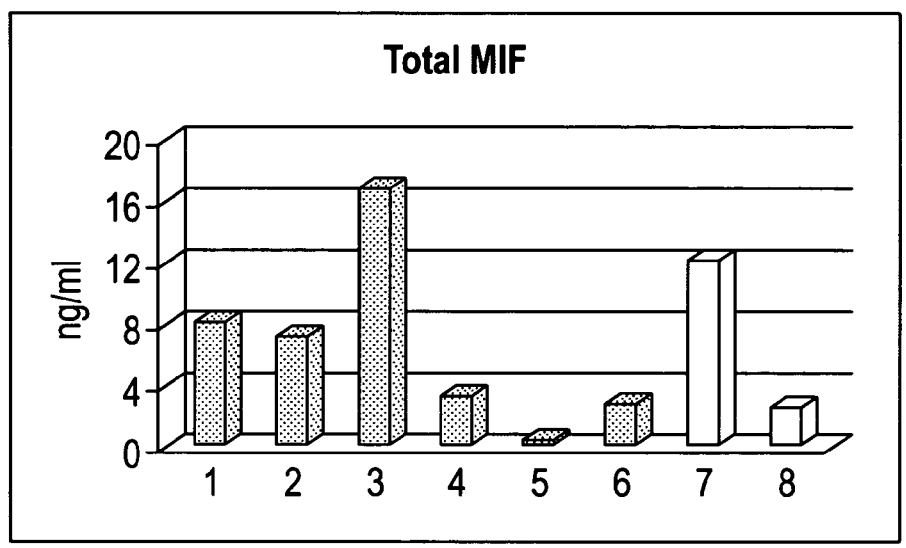
Figure 3:
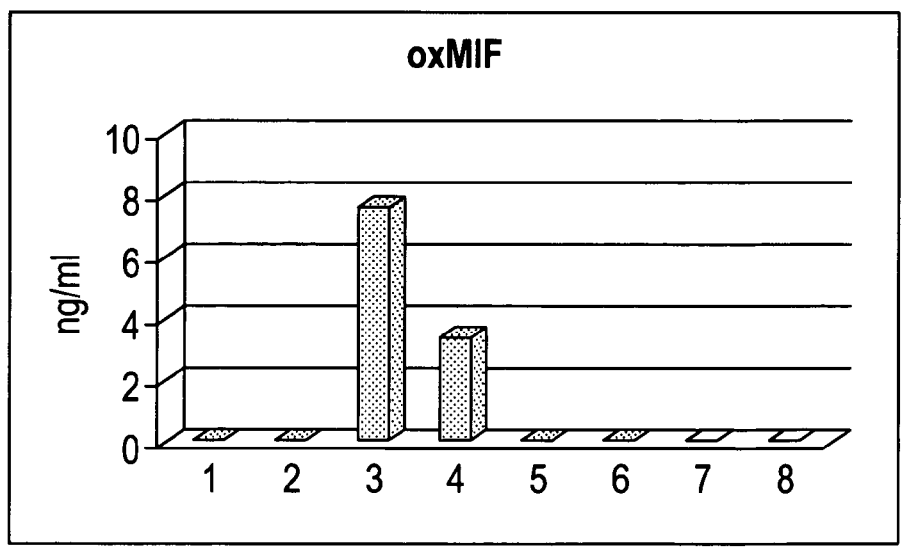

FIG. 3: Total MIF and oxMIF detection in plasma of bacteriemic patients

Total MIF and oxMIF levels in plasma from bacteriemic patients (1 to 6, black columns), one healthy control (7, grey column) and a pool of plasma from healthy donors (8, grey column) were assessed by ELISA.

Figure 4:
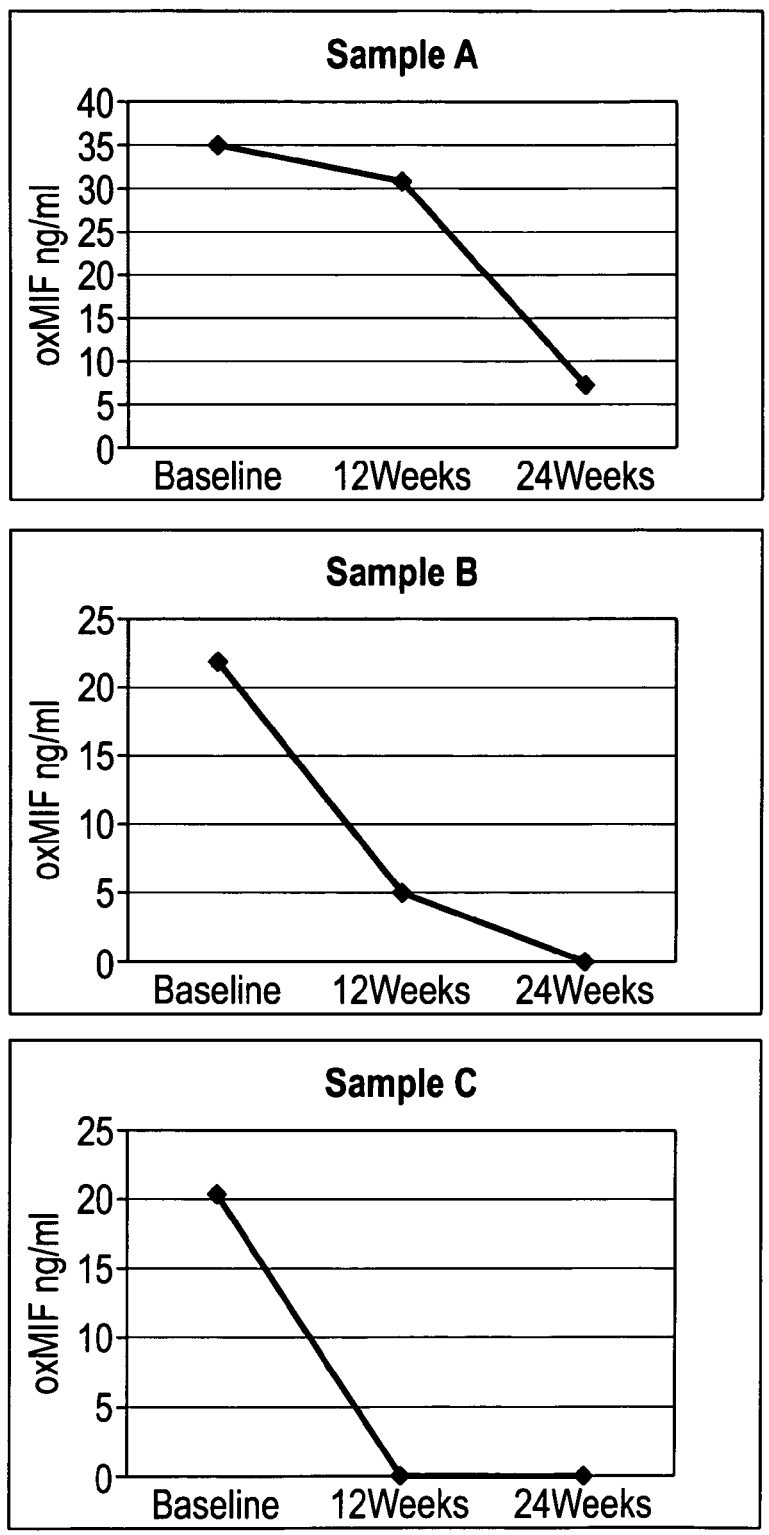

FIG. 4: Detection of oxMIF in serum samples of psoriasis patients.

Decrease of oxMIF levels in the circulation of the patients show correlation with the improvement of disease severity.

Figure 5:
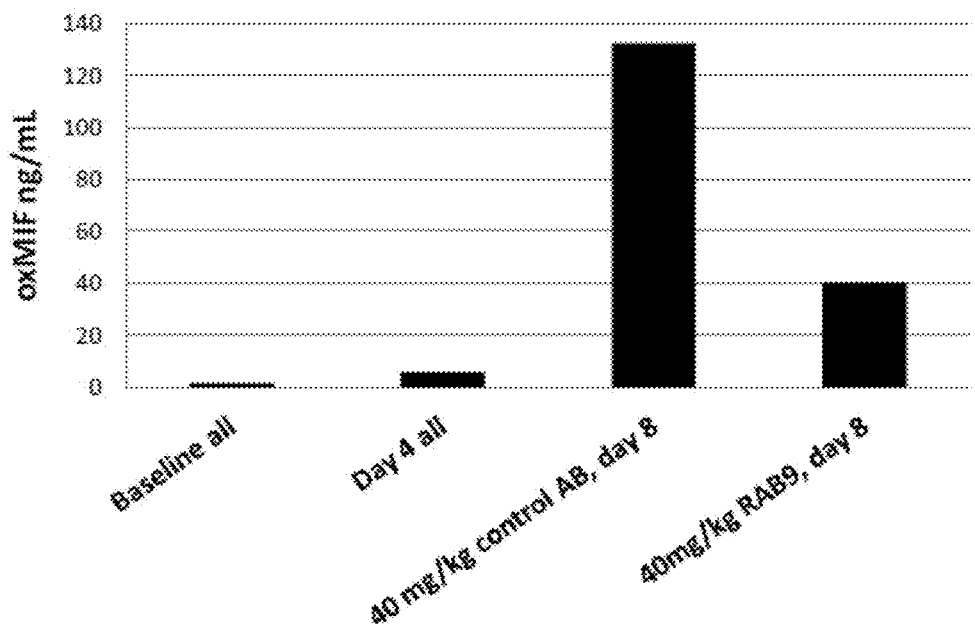
Figure 5:
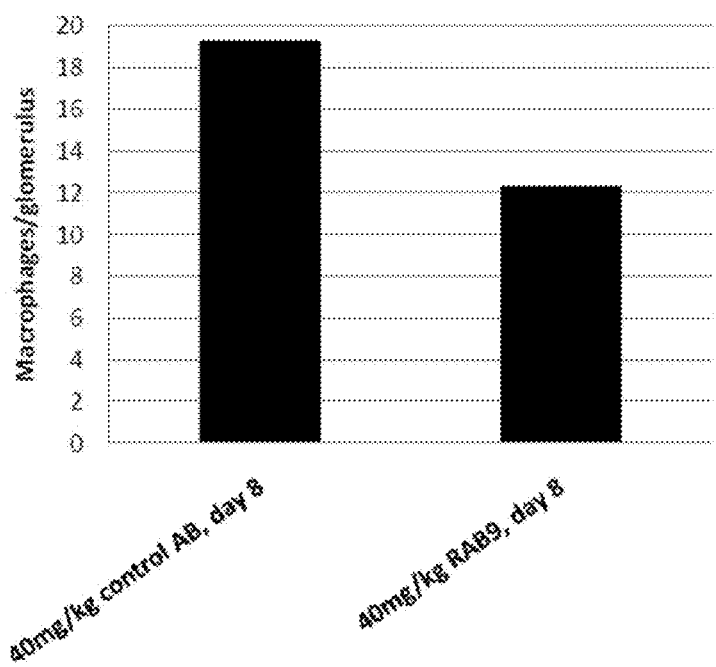

FIG. 5: Level of oxMIF in urine from rats with glomerulonephritis.

(A) Levels of oxMIF increase with disease progression from day 0 (before disease induction) to day 8 after disease induction. Treatment with anti-MIF antibody RAB9 reduces urinary levels of oxMIF on day 8. (3) Macrophage infiltration determined in the same experiment after sacrificing the animals on day 8. Reduced macrophage infiltration in the RAB9 treated group correlates with reduced oxMIF levels.

Figure 6A:
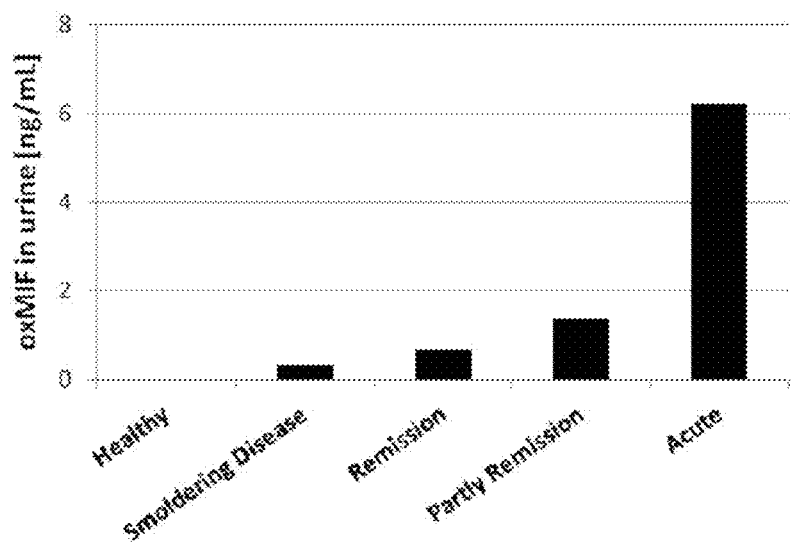
Figure 6B:
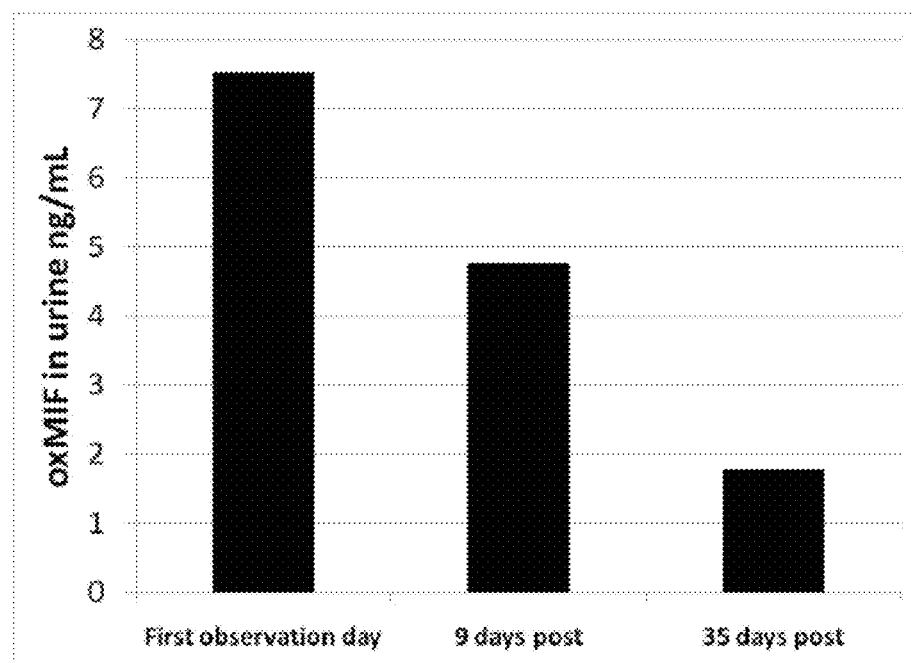

FIG. 6: Level of oxMIF in urine from patients with Lupus Nephritis.

(A) OxMIF levels in urine correlates with disease severity. Mean values measured for each patient group are shown. (B) Time course of oxMIF levels measured in one patient newly diagnosed with Lupus Nephritis. The patient was treated with unspecific immunosuppressive drugs and reduction of urinary oxMIF levels correlates with improved clinical situation. (C) OxMIF levels in the plasma correlates with disease severity. Mean values measured for each patient group are shown.

Figure 7:
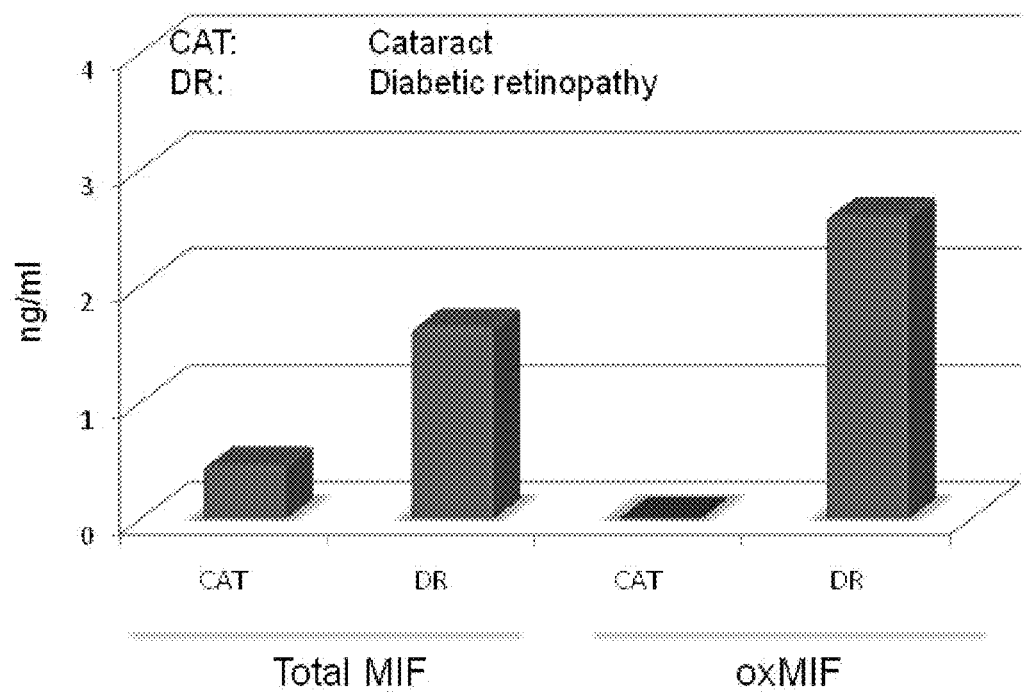
Figure 8A:
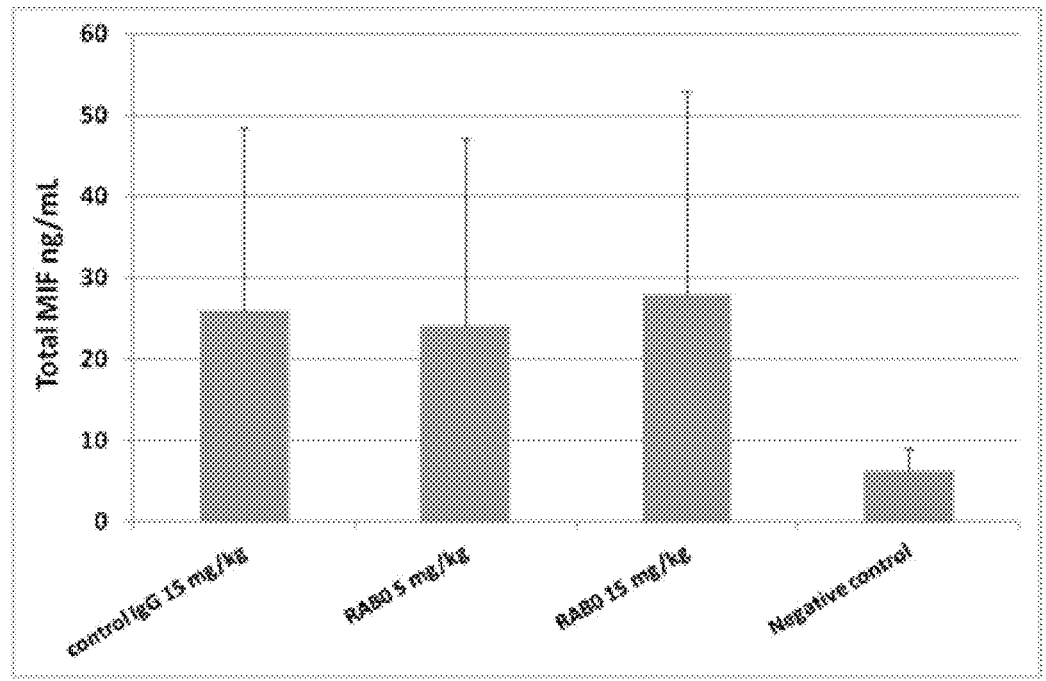

FIG. 7: Total MIF and oxMIF in the aqueous humor from patients with diabetic retinopathy Total MIF and oxMIF levels in aqueous humor obtained from patients with cataract (CAT, n=5) or diabetic retinopathy (DR, n=5) were assessed by ELISA FIG. 8: Xenograft mouse model for prostate cancer After termination of the animal model plasma samples from the mice have been taken to measure total MIF levels (A) as well as oxMIF levels (B). Tumors have been excised and weighed (C). The figures show the mean of the values obtained for each group. Plasma samples from non-xenografted mice were also analyzed for total MIF and oxMIF (=negative control).

Figure 9:
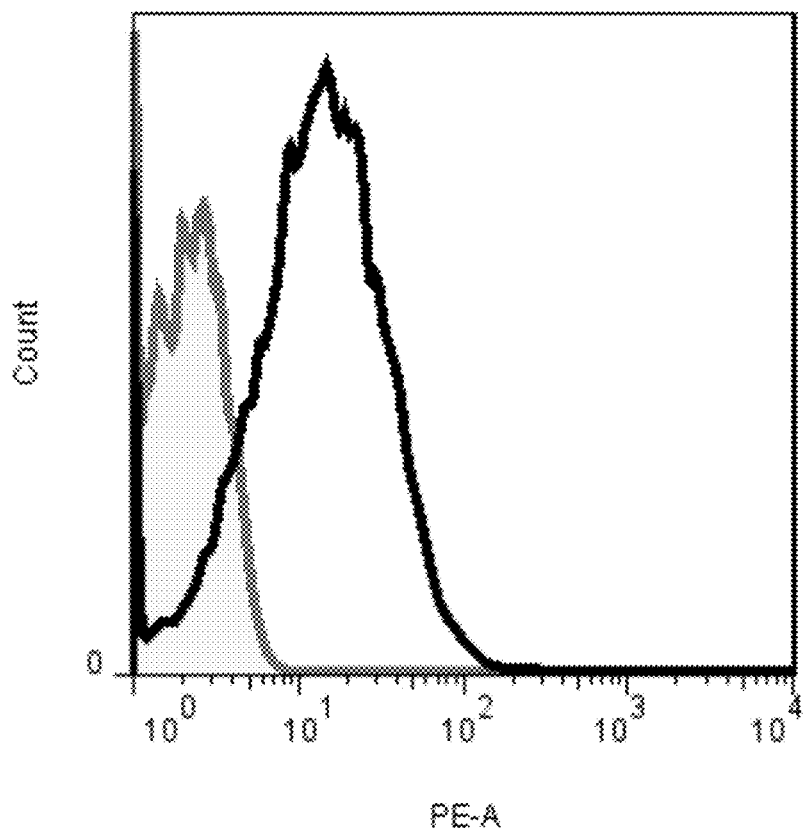

FIG. 9: oxMIF on the surface of the PC-3 prostate cancer cell line

PC-3 cells were first labelled with a control human IgG1 monoclonal antibody (grey tinted graph) and with RAB9 (black line). Detection of cell surface bound antibodies was done with an RPE-labelled rabbit anti-human IgG.

Figure 10:
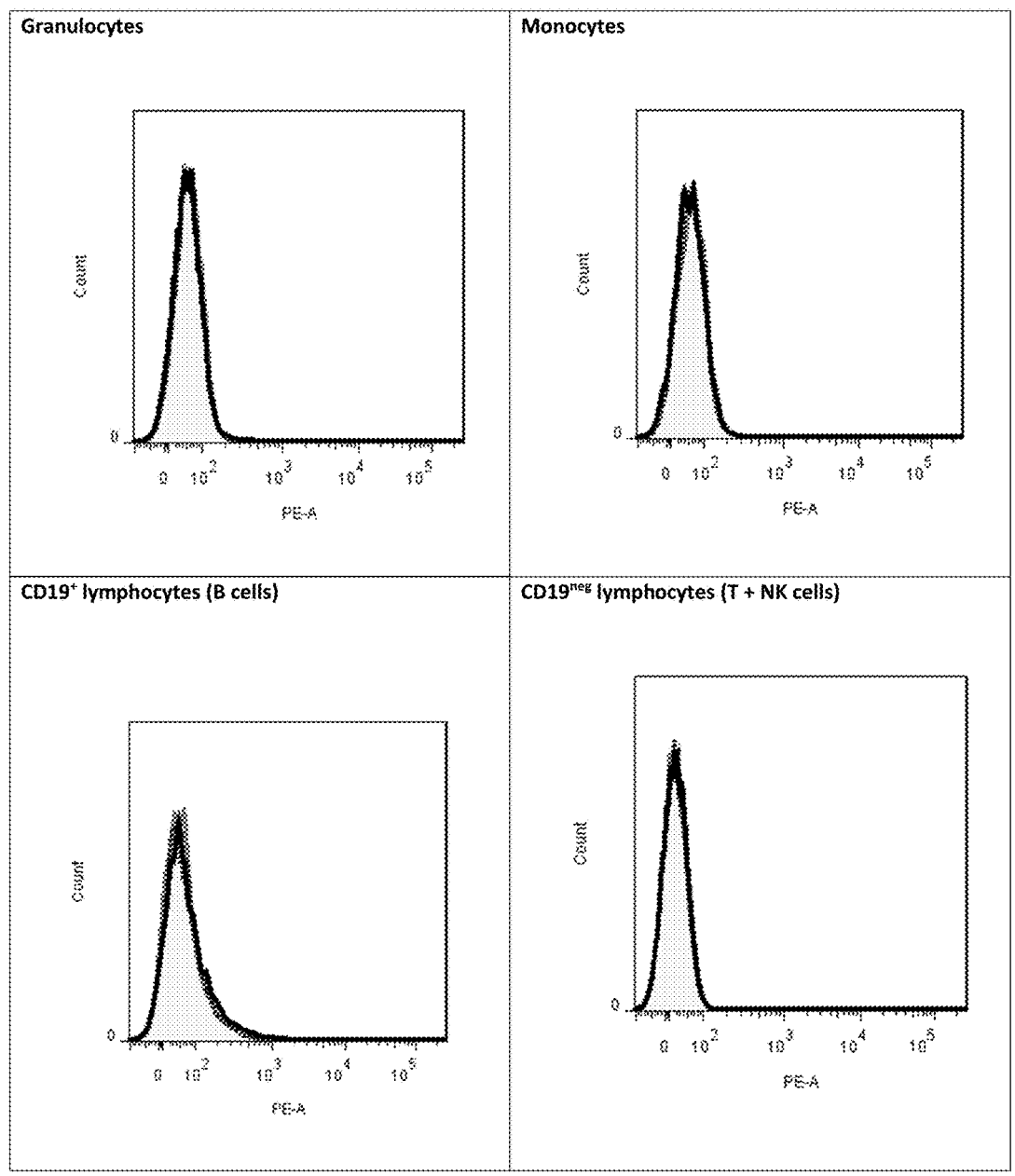

FIG. 10: Absence of oxMIF on the surface of leukocytes from healthy donors

Human blood cells from healthy donors were incubated with a control IgG1 human monoclonal antibody (grey tinted graph), with RAB9 (black line) or with RAB0 (black dotted line). Detection of cell surface bound antibodies was done with an RPE-labelled rabbit anti-human IgG. Electronic gating enabled us to distinguish between the granulocytes, monocytes, lymphocyte B cells (CD19$^+$ cells) and lymphocyte T cells+Natural Killer cells (CD19$^{neg}$ cells).

Figure 11:
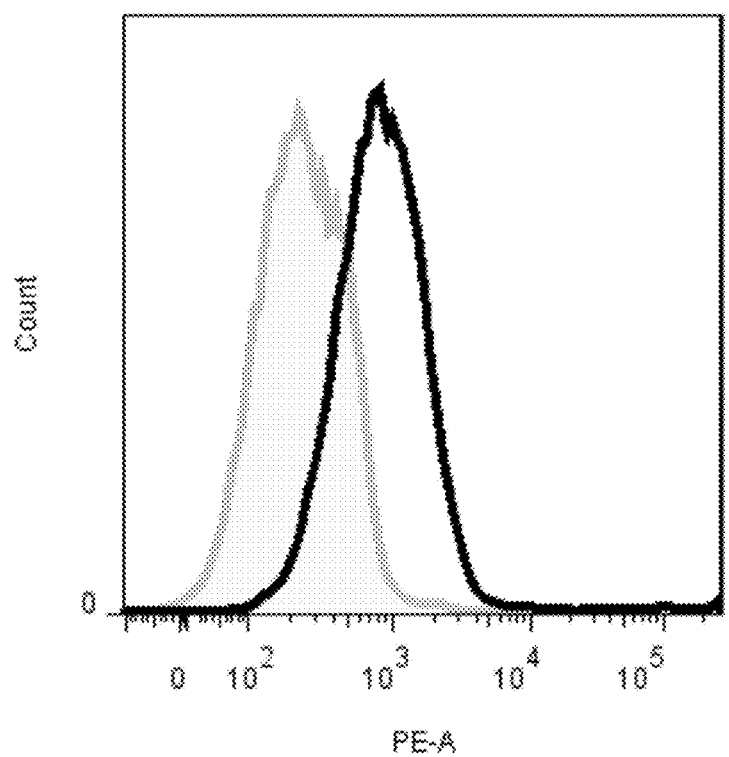

FIG. 11: oxMIF on the surface of the BxPC3 pancreatic cancer cell line

BxPC3 cells were first labelled with a control human IgG1 monoclonal antibody (grey tinted graph) or with RAB0 (black line). Detection of cell surface bound antibodies was done with an RPE-labelled rabbit anti-human IgG.

Figure 12:
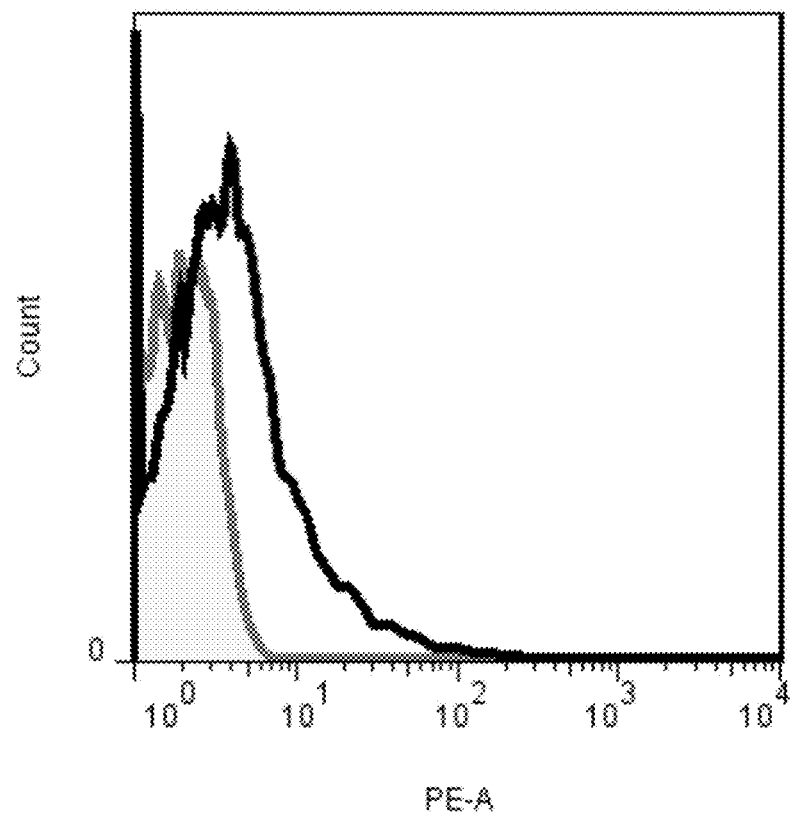

FIG. 12: oxMIF on the surface of the A2780 ovarian cancer cell line

A2780 cells were first labelled with a control human IgG1 monoclonal antibody (grey tinted graph), with RAB9 (black line). Detection of cell surface bound antibodies was done with an RPE-labelled rabbit anti-human IgG.

Figure 13:
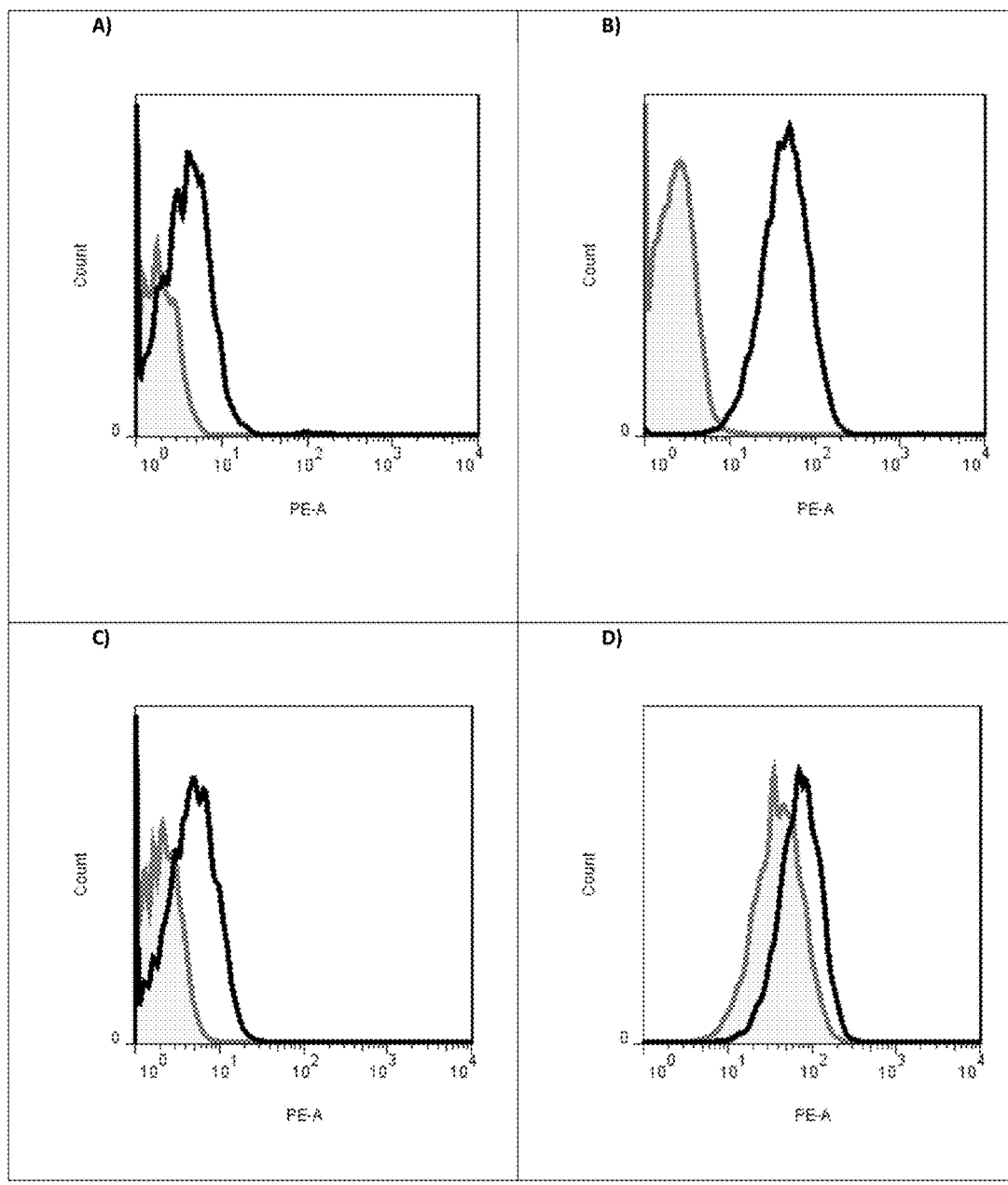

FIG. 13: oxMIF on the surface of human lymphoma cell line

Human lymphoma cell lines were first labelled with a control human IgG1 monoclonal antibody (grey tinted graph), with RAB9 (black line in A, B and D), or with RAB0 (black line in C). Detection of cell surface bound antibodies was done with an RPE-labelled rabbit anti-human IgG. A) CA46 Burkitt's lymphoma; B) MC-CAR B lymphocyte myeloma; C) Raji Burkitt's lymphoma; D) U937 histiocytic lymphoma.

Figure 14:
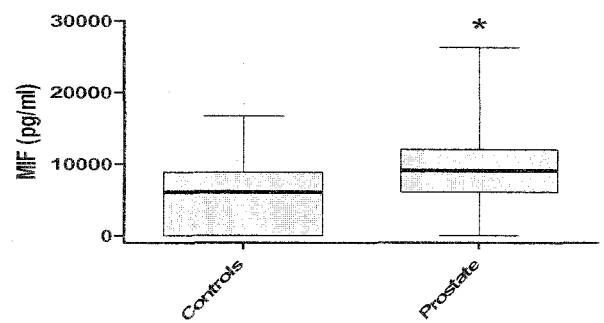
Figure 14:
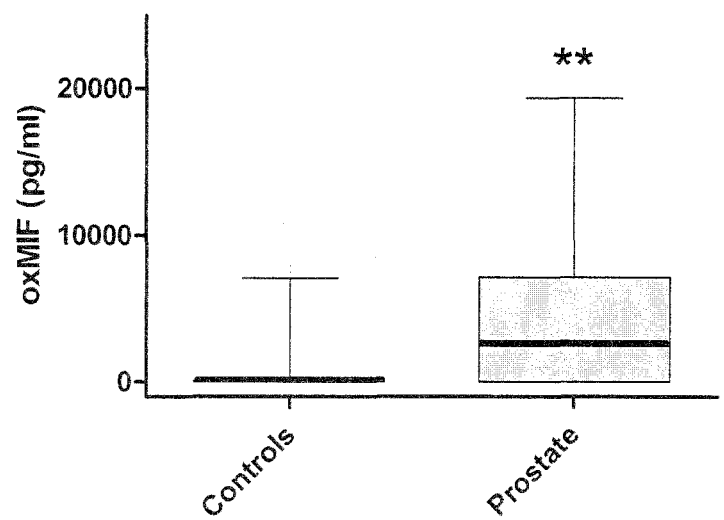
Figure 15:
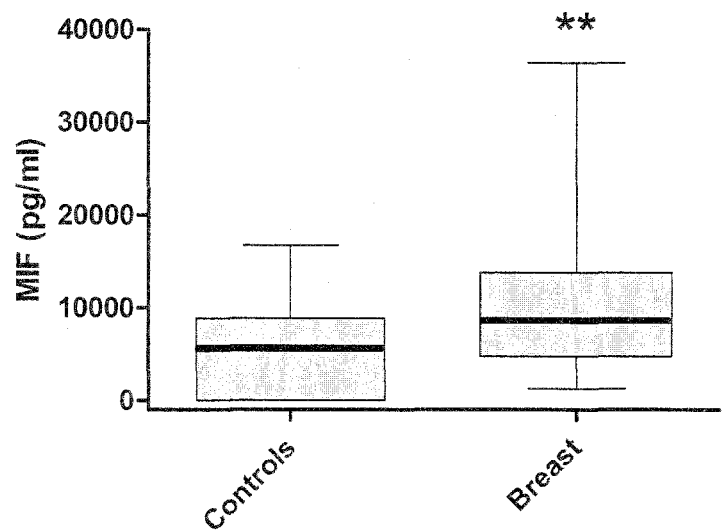
Figure 15:
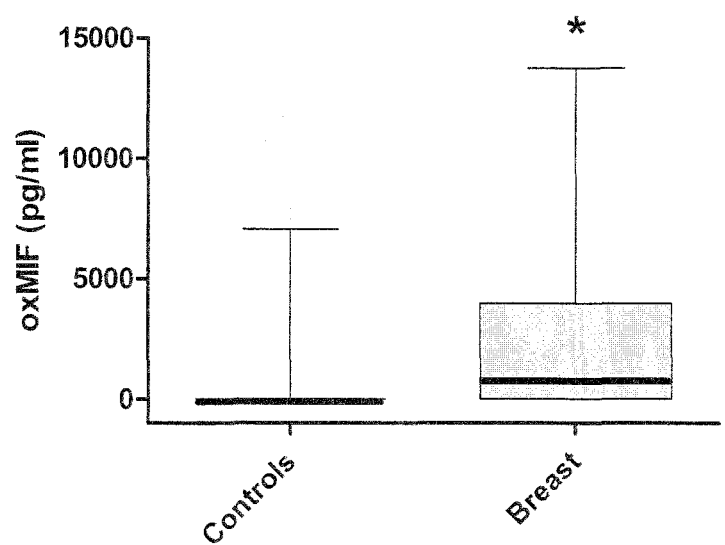
Figure 16:
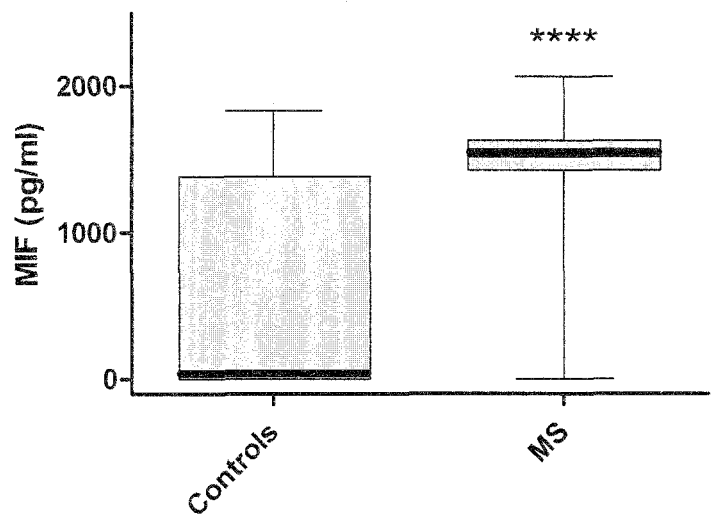
Figure 16:
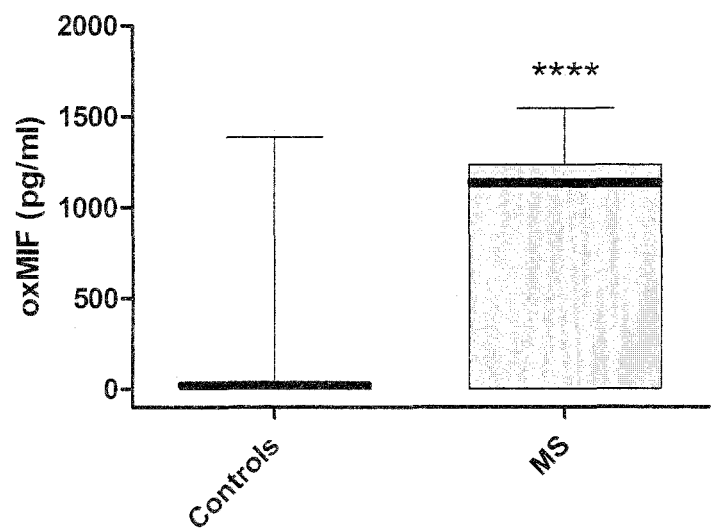

FIG. 14: Levels of total MIF and oxMIF in plasma from prostate cancer patients (A) Total MIF levels were measured in plasma from different prostate cancer patients (n=14) and from healthy volunteers (n=49). Box and whiskers (5-95% percentile) are shown with median in bold. Statistics: p=0.0166, t test unpaired one tail (B) oxMIF levels were measured in plasma from different prostate cancer patients (n=14) and from healthy volunteers (n=49). Box and whiskers (5-95% percentile) are shown with median in bold. Statistics: p=0.0016, t test unpaired one tail FIG. 15: Levels of total MIF and oxMIF in plasma from breast cancer patients (A) Total MIF levels were measured in plasma from different breast cancer patients (n=15) and from healthy volunteers (n=49). Box and whiskers (5-95% percentile) are shown with median in bold. Statistics: p=0.0078, t test unpaired one tail (B) oxMIF levels were measured in plasma from different breast cancer patients (n=15) and from healthy volunteers (n=49). Box and whiskers (5-95% percentile) are shown with median in bold. Statistics: p=0.0451, t test unpaired one tail FIG. 16: Levels of total MIF and oxMIF in cerebrospinal fluid from patients with multiple sclerosis
  (A) Total MIF levels were measured in cerebrospinal fluids from patients diagnosed with different forms of multiple sclerosis (n=49) and from healthy volunteers (n=30). Box and whiskers (5-95% percentile) are shown with medians (bold line). Statistics: p<0.0001, t test unpaired one tail
  (B) oxMIF levels were measured in cerebrospinal fluids from patients diagnosed with different forms of multiple sclerosis (n=49) and from healthy volunteers (n=30). Box and whiskers (5-95% percentile) are shown with medians (bold line). Statistics: p<0.0001, t test unpaired one tail FIG. 17: Levels of total MIF and oxMIF in plasma from ovarian cancer patients
  (A) Total MIF levels were measured in plasma from different ovarian cancer patients (n=42) and from healthy volunteers (n=19). Box and whiskers (5-95% percentile) are shown with median in bold. Statistics: p=0.0434, t test unpaired one tail
  (B) oxMIF levels were measured in plasma from different ovarian cancer patients (n=42) and from healthy volunteers (n=19). Box and whiskers (5-95% percentile) are shown with median in bold. Statistics: p=0.0663, t test unpaired one tail
  (C) Total MIF levels were measured in plasma from different kind of ovarian cancer patients (clear cell adenocarcinoma n=7, papillary serous cystadenocarcinoma n=14, and serous cystadenocarcinoma n=21) and from healthy volunteers (n=19). Box and whiskers (5-95% percentile) are shown with median in bold. Statistical significance was assessed using the t test (unpaired one tail) for each group against the control group:
    a. Controls (n=19) vs Clear Cell Adenocarcinoma (n=7): p=0.3696
    b. Controls (n=19) vs Papillary Serous Cystadenocarcinoma (n=14): p=0.0721
    c. Controls (n=19) vs Serous Cystadenocarcinoma (n=21): p=0.0046**
  (D) oxMIF levels were measured in plasma from different kind of ovarian cancer patients (clear cell adenocarcinoma n=7, papillary serous cystadenocarcinoma n=14, and serous cystadenocarcinoma n=21) and from healthy volunteers (n=19). Box and whiskers (5-95% percentile) are shown with median in bold. Statistical significance was assessed using the t test (unpaired one tail) for each group against the control group:
    a. Controls (n=19) vs Clear Cell Adenocarcinoma (n=7): p=0.4518
    b. Controls (n=19) vs Papillary Serous Cystadenocarcinoma (n=14): p=0.0438*
    c. Controls (n=19) vs Serous Cystadenocarcinoma (n=21): p=0.0357*

FIG. 17A: Levels of total MIF in plasma from ovarian cancer patients

FIG. 17B: Levels of oxMIF in plasma from ovarian cancer patients

Figure 17C:
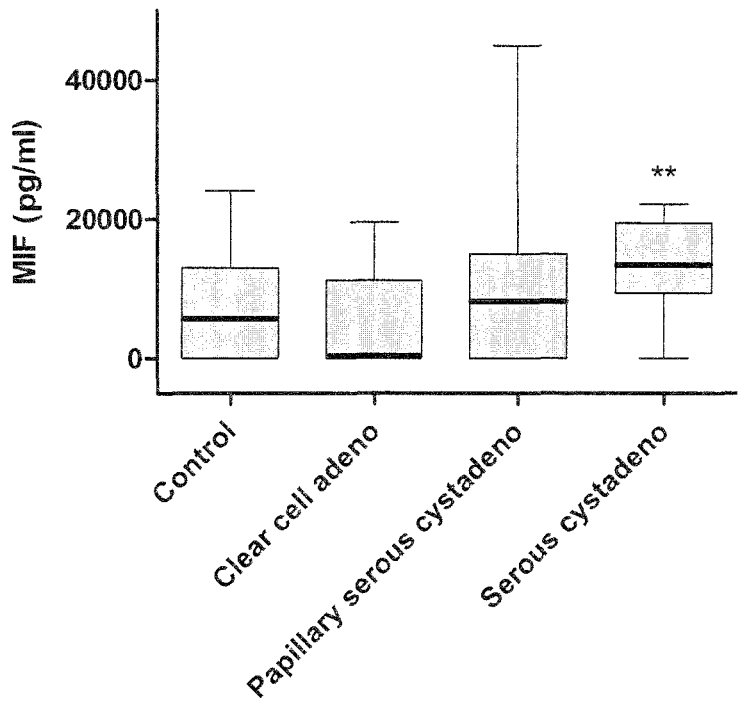
Figure 17D:
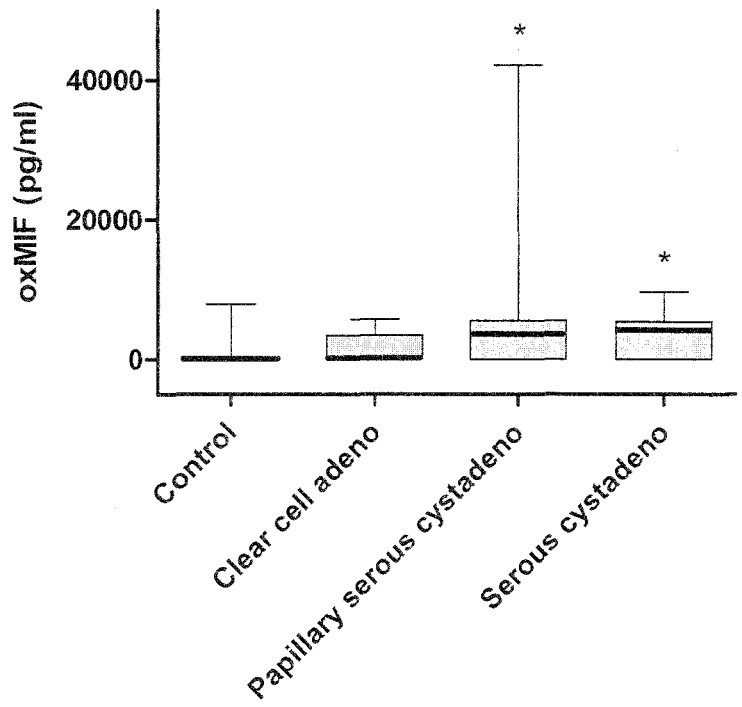

FIG. 17C: Levels of total MIF in plasma from patients with different forms of ovarian cancer FIG. 17D: Levels of oxMIF in plasma from patients with different forms of ovarian cancer FIG. 18: Levels of total MIF and oxMIF in plasma from UC and CD patients
  (A) Total MIF levels were measured in plasma from different UC (n=15) and CD patients (n=21), as well as from healthy volunteers (n=19). Box and whiskers (5-95% percentile) are shown with median in bold.
    a. Controls vs UC: p=0.1240, t test unpaired one tail
    b. Controls vs CD: p=0.0207*, t test unpaired one tail
  (B) oxMIF levels were measured in plasma from different UC (n=15) and CD patients (n=21), as well as from healthy volunteers (n=19). Box and whiskers (5-95% percentile) are shown with median in bold.
    a. Controls vs UC: p=0.0417*, t test unpaired one tail
    b. Controls vs CD: p=0.0114*, t test unpaired one tail FIG. 18A: Levels of total MIF in plasma from patients with UC and CD FIG. 18B: Levels of oxMIF in plasma from patients with UC and CD

DEFINITIONS AND GENERAL TECHNIQUES

Unless otherwise defined herein, scientific and technical terms used in connection with the present invention shall have the meanings that are commonly understood by those of ordinary skill in the art. Generally, nomenclatures used in connection with, and techniques of, cell and tissue culture, molecular biology, immunology, microbiology, genetics and protein and nucleic acid chemistry described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), which are incorporated herein by reference.

"MIF" or "macrophage migration inhibitory factor" refers to the protein, which is known as a critical mediator in the immune and inflammatory response, and as a counterregulator of glucocorticoids. MIF includes mammalian MIF, specifically human MIF (Swiss-Prot primary accession number: P14174), wherein the monomeric form is encoded as a 115 amino acid protein but is produced as a 114 amino acid protein due to cleavage of the initial methionine. "MIF" also includes "GIF" (glycosylation-inhibiting factor) and other forms of MIF such as fusion proteins of MIF. The numbering of the amino acids of MIF starts with the N-terminal methionine (amino acid 1) and ends with the C-terminal alanine (amino acid 115).

"oxidized MIF" or oxMIF is defined for the purposes of the invention as an isoform of MIF that occurs by treatment of MIF with mild oxidizing reagents, such as Cystine. As has been shown by the present invention, recombinant oxMIF that has been treated this way comprises isoform(s) of MIF that share structural rearrangements with oxMIF that (e.g.) occurs in vivo after challenge of animals with bacteria.

redMIF is defined for the purposes of this invention as reduced MIF and is MIF which does not bind to RAB0, RAB9 and/or RAB4.

The anti-oxMIF antibodies described in this invention are able to discriminate between ox and red MIF, which are generated by mild oxidation or reduction, respectively, and are useful to specifically detect oxMIF. Discrimination between these conformers is assessed by ELISA (e.g. as described in example 3.4) or surface plasmon resonance.

Assessing Differential Binding of the Antibodies by Biacore.

Binding kinetics of oxMIF and redMIF to antibody RAB9 and RAB0 are examined by surface plasmon resonance analysis using a Biacore 3000 System. The antibodies were coated on a CM5 (=carboxymethylated dextran) chip and recombinant MIF protein, pre-incubated with 0.2% Proclin300, were injected. (Proclin300 consists of oxidative isothiazolones that stabilize the oxMIF structure by avoiding a conversion of oxMIF to redMIF). In native HES-EP buffer (=Biacore running buffer) without addition of ProClin300, none of the recombinant MIF proteins bound to RAB9, RAB0 or to the reference antibody (irrelevant isotype control antibody) used as negative (background) binding control.

In a preferred embodiment, oxMIF is MIF which is differentially bound by antibody RAB9, RAB4 and/or RAB0 or an antigen-binding fragment thereof, meaning that these antibodies do bind to oxMIF while redMIF is not bound by either one of these antibodies.

In other embodiments, the anti-oxMIF antibodies, e.g. the antibodies mentioned above or an antigen-binding portion thereof bind oxMIF with a $K_D$ of less than 100 nM, preferably a $K_D$ of less than 50 nM, even more preferred with a $M_D$ of less than 10 nM. Particularly preferred, the antibodies of this invention bind to oxMIF with a $M_D$ of less than 5 nM.

(Non-)binding of an antibody, e.g. RAB9, RAB4 or RAB0 (to oxMIF or redMIF) can be determined as generally known to a person skilled in the art, examples being any one of the following methods: Differential Binding ELISA with recombinant MIF, or surface plasmon resonance using recombinant MIF in its reduced or oxidized state, like the well known Biacore assay, described above.

A preferred method for the determination of binding is surface plasmon resonance of an antibody to e.g. rec. (ox)MIF whereupon "binding" is meant to be represented by a $K_D$ of less than 100 nM preferably less than 50 nM, even more preferred less than 10 nM whereas the non-binding to redMIF is characterized by a $K_D$ of more than 400 nM. "Binding" and "specific binding" is used interchangeably here to denote the above. "Differential binding" in the context of this application means that a compound, in particular the antibodies as described herein, bind to oxMIF (e.g. with the $K_D$ values mentioned above) while they do not bind to redMIF (with non-binding again being defined as above).

An "antibody" refers to an intact antibody or an antigen-binding portion that competes with the intact antibody for (specific) binding. See generally, Fundamental Immunology, Ch. 7 (Paul, W., ed., 2nd ed. Raven Press, N.Y. (1989)) (incorporated by reference). The term antibody includes human antibodies, mammalian antibodies, isolated antibodies and genetically engineered forms such as chimeric, camelized or humanized antibodies, though not being limited thereto.

The term "antigen-binding portion" of an antibody refers to one or more fragments of an antibody that retain the ability to specifically bind to an antigen (e.g. (ox)MIF). Antigen-binding portions may be produced by recombinant DNA techniques or by enzymatic or chemical cleavage of intact antibodies. Antigen-binding portions include e.g.— though not limited thereto—the following: Fab, Fab', F(ab')2, Fv, and complementarity determining region (CDR) fragments, single-chain antibodies (scFv), chimeric antibodies, antibodies and polypeptides that contain at least a portion of an antibody that is sufficient to confer specific antigen binding to the polypeptide, i.e. ox or redMIF. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia et al. J. Mol. Biol. 196:901-917 (1987), or Chothia et al., Nature 342:878-883 (1989). An antibody or antigen-binding portion thereof can be derivatized or linked to another functional molecule (e.g., another peptide or protein). For example, an antibody or antigen-binding portion thereof can be functionally linked to one or more other molecular entities, such as another antibody (e.g., a bispecific antibody or a diabody), a detectable agent, a cytotoxic agent, a pharmaceutical agent, and/or a linking molecule.

The term "KD" refers here, in accordance with the general knowledge of a person skilled in the art to the equilibrium dissociation constant of a particular antibody with the respective antigen. This equilibrium dissociation constant measures the propensity of a larger object (here: complex ox or red MIF/antibody) to separate, i.e. dissociate into smaller components (here: ox or redMIF and antibody).

The term "human antibody" refers to any antibody in which the variable and constant domains are human sequences. The term encompasses antibodies with sequences derived from human genes, but which have been changed, e.g. to decrease possible immunogenicity, increase affinity, eliminate cysteines that might cause undesirable folding, etc. The term encompasses such antibodies produced recombinantly in non-human cells, which might e.g. impart glycosylation not typical of human cells.

The term "humanized antibody" refers to antibodies comprising human sequences and containing also non-human sequences.

The term "camelized antibody" refers to antibodies wherein the antibody structure or sequences has been changed to more closely resemble antibodies from camels, also designated camelid antibodies. Methods for the design and production of camelized antibodies are part of the general knowledge of a person skilled in the art.

The term "chimeric antibody" refers to an antibody that comprises regions from two or more different species.

The term "isolated antibody" or "isolated antigen-binding portion thereof" refers to an antibody or an antigen-binding portion thereof that has been identified and selected from an antibody source such as a phage display library or a B-cell repertoire.

The production of the anti-(ox)MIF antibodies according to the present invention includes any method for the generation of recombinant DNA by genetic engineering, e.g. via reverse transcription of RNA and/or amplification of DNA and cloning into expression vectors. In some embodiments, the vector is a viral vector, wherein additional DNA segments may be ligated into the viral genome. In some embodiments, the vector is capable of autonomous replication in a host cell into which it is introduced (e.g. bacterial vectors having a bacterial origin of replication and episomal mammalian vectors). In other embodiments, the vector (e.g. non-episomal mammalian vectors) can be integrated into the genome of a host cell upon introduction into the host cell, and thereby replicated along with the host genome. Moreover, certain vectors are capable of directing the expression of genes to which they are operatively linked. Such vectors are referred to herein as "recombinant expression vectors" (or simply, "expression vectors").

Anti-(ox)MIF antibodies can be produced inter alia by means of conventional expression vectors, such as bacterial vectors (e.g., pBR322 and its derivatives), or eukaryotic vectors. Those sequences that encode the antibody can be provided with regulatory sequences that regulate the replication, expression and/or secretion from the host cell. These regulatory sequences comprise, for instance, promoters (e.g., CMV or SV40) and signal sequences. The expression vectors can also comprise selection and amplification markers, such as the dihydrofolate reductase gene (DHFR), hygromycin-B-phosphotransferase, and thymidine-kinase. The components of the vectors used, such as selection markers, replicons, enhancers, can either be commercially obtained or prepared by means of conventional methods. The vectors can be constructed for the expression in various cell cultures, e.g., in mammalian cells such as CHO, COS, HEK293, NSO, fibroblasts, insect cells, yeast or bacteria such as E. coli. In some instances, cells are used that allow for optimal glycosylation of the expressed protein.

The anti-(ox)MIF antibody light chain gene(s) and the anti-(ox)MIF antibody heavy chain gene(s) can be inserted into separate vectors or the genes are inserted into the same expression vector. The antibody genes are inserted into the expression vector by standard methods, e.g., ligation of complementary restriction sites on the antibody gene fragment and vector, or blunt end ligation if no restriction sites are present.

The production of anti-(ox)MIF antibodies or antigen-binding fragments thereof may include any method known in the art for the introduction of recombinant DNA into eukaryotic cells by transfection, e.g. via electroporation or microinjection. For example, the recombinant expression of anti-(ox)MIF antibody can be achieved by introducing an expression plasmid containing the anti-(ox)MIF antibody encoding DNA sequence under the control of one or more regulating sequences such as a strong promoter, into a suitable host cell line, by an appropriate transfection method resulting in cells having the introduced sequences stably integrated into the genome. The lipofection method is an example of a transfection method which may be used according to the present invention.

The production of anti-(ox)MIF antibodies may also include any method known in the art for the cultivation of said transformed cells, e.g. in a continuous or batchwise manner, and the expression of the anti-(ox)MIF antibody, e.g. constitutive or upon induction. It is referred in particular to WO 2009/086920 for further reference for the production of anti-(ox)MIF antibodies. In a preferred embodiment, the anti-(ox)MIF antibodies as produced according to the present invention bind to oxMIF or an epitope thereof. Particularly preferred antibodies in accordance with the present invention are antibodies RAB9, RAB4 and/or RAB0 as well as RAM9, RAM4 and/or RAM0.

The sequences of these antibodies are partly also disclosed in WO 2009/086920; see in addition the sequence list of the present application and the following:

```
SEQ ID NO: 1 for the amino acid sequence
of the light chain of RAB9:
DIQMTQSPSS LSASVGDRVT ITCRSSQRIM TYLNWYQQKP

GKAPKLLIFV ASHSQSGVPS RFRGSGSETD FTLTISGLQP

EDSATYYCQQ SFWTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 2 for the amino acid sequence
of the light chain of RAB4:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 3 for the amino acid sequence
of the light chain of RAB0:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 4 for the amino acid sequence
of the light chain of RAB2:
DIQMTQSPVT LSLSPGERAT LSCRASQSVR SSYLAWYQQK

PGQTPRLLIY GASNRATGIP DRFSGSGSGT DFTLTISRLE

PEDFAVYYCQ QYGNSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC,

SEQ ID NO: 5 for the amino acid sequence
of the heavy chain of RAB9:
EVQLLESGGG LVQPGGSLRL SCAASGFTFS IYSMNWVRQA

PGKGLEWVSS IGSSGGTTYY ADSVKGRFTI SRDNSKNTLY

LQMNSLRAED TAVYYCAGSQ WLYGMDVWGQ GTTVTVSSAS

TKGPSVFPLA PCSRSTSEST AALGCLVKDY FPEPVTVSWN

SGALTSGVHT FPAVLQSSGL YSLSSVVTVP SSSLGTKTYT

CNVDHKPSNT KVDKRVESKY GPPCPPCPAP EFLGGPSVFL

FPPKPKDTLM ISRTPEVTCV VVDVSQEDPE VQFNWYVDGV

EVHNAKTKPR EEQFNSTYRV VSVLTVLHQD WLNGKEYKCK

VSNKGLPSSI EKTISKAKGQ PREPQVYTLP PSQEEMTKNQ

VSLTCLVKGF YPSDIAVEWE SNGQPENNYK TTPPVLDSDG

SFFLYSRLTV DKSRWQEGNV FSCSVMHEAL HNHYTQKSLS

LSLGK,

SEQ ID NO: 6 for the amino acid sequence
of the heavy chain of RAB4:
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS
```

-continued
SSLGTKTYTC NVDHKPSNTK VDKRVESKYG PPCPPCPAPE

FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK,

SEQ ID NO: 7 for the amino acid sequence
of the heavy chain of RAB0:
EVQLLESGGG LVQPGGSLRL SCAASGFTFS WYAMDWVRQA

PGKGLEWVSG IYPSGGRTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS

SSLGTKTYTC NVDHKPSNTK VDKRVESKYG PPCPPCPAPE

FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK,

SEQ ID NO: 8 for the amino acid sequence
of the heavy chain of RAB2:
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP CSRSTSESTA ALGCLVKDYF

PEPVTVSWNS GALTSGVHTF PAVLQSSGLY SLSSVVTVPS

SSLGTKTYTC NVDHKPSNTK VDKRVESKYG PPCPPCPAPE

FLGGPSVFLF PPKPKDTLMI SRTPEVTCVV VDVSQEDPEV

QFNWYVDGVE VHNAKTKPRE EQFNSTYRVV SVLTVLHQDW

LNGKEYKCKV SNKGLPSSIE KTISKAKGQP REPQVYTLPP

SQEEMTKNQV SLTCLVKGFY PSDIAVEWES NGQPENNYKT

TPPVLDSDGS FFLYSRLTVD KSRWQEGNVF SCSVMHEALH

NHYTQKSLSL SLGK.

SEQ ID NO: 9 for the amino acid sequence
of RAM0hc:
EVQLLESGGG LVQPGGSLRL SCAASGFTFS WYAMDWVRQA

PGKGLEWVSG IYPSGGRTKY ADSVKGRFTI SRDNSKNTLY

LQMNSLRAED TAVYYCARVN VIAVAGTGYY YYGMDVWGQG

TTVTVSSAST KGPSVFPLAP SSKSTSGGTA ALGCLVKDYF

PEPVTVSWNS GALTSGVHTF PAVLQSSGLY SLSSVVTVPS

SSLGTQTYIC NVNHKPSNTK VDKRVEPKSC DKTHTCPPCP

APELLGGPSV FLFPPKPKDT LMISRTPEVT CVVVDVSNED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK.

SEQ ID NO: 10 for the amino acid sequence
of RAM0lc:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.

SEQ ID NO: 11 for the amino acid sequence
of RAM9hc:
EVQLLESGGG LVQPGGSLRL SCAASGFTFS IYSMNWVRQA

PGKGLEWVSS IGSSGGTTYY ADSVKGRFTI SRDNSKNTLY

LQMNSLRAED TAVYYCAGSQ WLYGMDVWGQ GTTVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPELLGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLTCLV KGFYPSDIAV EWESNGQPEN NYKTTPPVLD

SDGSFFLYSK LTVDKSRWQQ GNVFSCSVMH EALHNHYTQK

SLSLSPGK.

SEQ ID NO: 12 for the amino acid sequence
of RAM9lc:
DIQMTQSPSS LSASVGDRVT ITCRSSQRIM TYLNWYQQKP

GKAPKLLIFV ASHSQSGVPS RFRGSGSETD FTLTISGLQP

EDSATYYCQQ SFWTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.

SEQ ID NO: 13 for the amino acid sequence
of RAM4hc:
EVQLLESGGG LVQPGGSLRL SCAASGFTFS IYAMDWVRQA

PGKGLEWVSG IVPSGGFTKY ADSVKGRFTI SRDNSKNTLY

LQMNSLRAED TAVYYCARVN VIAVAGTGYY YYGMDVWGQG

TTVTVSSAST KGPSVFPLAP SSKSTSGGTA ALGCLVKDYF

PEPVTVSWNS GALTSGVHTF PAVLQSSGLY SLSSVVTVPS

SSLGTQTYIC NVNHKPSNTK VDKRVEPKSC DKTHTCPPCP

APELLGGPSV FLFPPKPKDT LMISRTPEVT CVVVDVSHED

```
                 -continued
PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK.

SEQ ID NO: 14 for the amino acid sequence
of RAM41c:
DIQMTQSPGT LSLSPGERAT LSCRASQGVS SSSLAWYQQK

PGQAPRLLIY GTSSRATGIP DRFSGSASGT DFTLTISRLQ

PEDFAVYYCQ QYGRSLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.
```

The anti-MIF antibody of the invention is preferably an isolated monoclonal antibody. The anti-MIF antibody can be an IgG, an IgM, an IgE, an IgA, or an IgD molecule. In other embodiments, the anti-MIF antibody is an IgG1, IgG2, IgG3 or IgG4 subclass. In other embodiments, the antibody is either subclass IgG1 or IgG4. In other embodiments, the antibody is subclass IgG4. In some embodiments, the IgG4 antibody has a single mutation changing the serine (serine-228, according to the Kabat numbering scheme) to proline. Accordingly, the CPSC sub-sequence in the Fc region of IgG4 becomes CPPC, which is a sub-sequence in IgG1 (Angal et al. Mol. Immunol. 1993, 30, 105-108).

Additionally, the production of anti-(ox)MIF antibodies may include any method known in the art for the purification of an antibody, e.g. via anion exchange chromatography or affinity chromatography. In one embodiment the anti-(ox) MIF antibody can be purified from cell culture supernatants by size exclusion chromatography.

The terms "center region" and "C-terminal region" of MIF refer to the region of human MIF comprising amino acids 35-68 and as 86-115, respectively, preferably as 50-68 and as 86 to 102 of human MIF, respectively.

Particularly preferred antibodies of the present invention bind to either region as 50-68 or region as 86-102 of human MIF. This is also reflected by the binding of the preferred antibodies RAB0, RAB4 RAB2 and RAB9 as well as RAM4, RAM9 and RAM0 which bind as follows:
  RAB4 and RAM4: as 86-102
  RAB9 and RAM9: as 50-68
  RAB0 and RAM0: as 86-102
  RAB2: as 86-102

The term "epitope" includes any protein determinant capable of specific binding to an immunoglobulin or an antibody fragment. Epitopic determinants usually consist of chemically active surface groupings of molecules such as exposed amino acids, amino sugars, or other carbohydrate side chains and usually have specific three-dimensional structural characteristics, as well as specific charge characteristics.

The term "vector" refers to a nucleic acid molecule capable of transporting another nucleic acid to which it has been linked. In some embodiments, the vector is a plasmid, i.e., a circular double stranded DNA loop into which additional DNA segments may be ligated.

The term "host cell" refers to a cell line, which is capable to produce a recombinant protein after introducing an expression vector. The term "recombinant cell line", refers to a cell line into which a recombinant expression vector has been introduced. It should be understood that "recombinant cell line" means not only the particular subject cell line but also the progeny of such a cell line. Because certain modifications may occur in succeeding generations due to either mutation or environmental influences, such progeny may not, in fact, be identical to the parent cell, but are still included within the scope of the term "recombinant cell line" as used herein.

The host cell type according to the present invention is e.g. a COS cell, a CHO cell or e.g. an HEK293 cell, or any other host cell known to a person skilled in the art, thus also for example including bacterial cells, like e.g. E. coli cells. In one embodiment, the anti-MIF antibody is expressed in a DHFR-deficient CHO cell line, e.g., DXE11, and with the addition of G418 as a selection marker. When recombinant expression vectors encoding antibody genes are introduced into CHO host cells, the antibodies are produced by culturing the host cells for a period of time sufficient to allow for expression of the antibody in the host cells or secretion of the antibody into the culture medium in which the host cells are grown.

Anti-(ox)MIF antibodies can be recovered from the culture medium using standard protein purification methods.

A "MIF-related, disease" in the present context refers generally to infectious diseases, inflammation, autoimmunity, cancer, cell differentiation and atherogenesis. MIF-related diseases are e.g., type I and II-diabetes, acute lung injury, asthma, allograft-rejection, graft-versus-host-disease, wound healing disturbances and inflammatory bowel disease. Further, cancer is a MIF-related disease. In particular, MIF-related cancers are lymphoma, sarcoma, prostatic cancer and colon cancer, bladder cancer, pancreas cancer, ovarian cancer, melanoma, hepatocellular carcinoma, ovarian cancer, breast cancer and pancreatic cancer.

Further, atherosclerosis is a MIF-related disease.

Further MIF-related diseases are sarcoidosis, scleroderma, psoriasis, (ulcerative) colitis, as well atopic dermatitis, as well as septic shock, delayed hypersensitivity, acute respiratory distress syndrome (ARDS), multiple sclerosis, pancreatitis and ischemic cardiac injury.

Immune and inflammatory disorders, which are MIF-related, are gram negative and gram positive sepsis, e.g. P. aeruginosa infections or sepsis, DTH, glomerulonephritis, arthritis, adjuvant arthritis, juvenile arthritis, (autoimmune) encephalomyelitis/encephalitis, (autoimmune) myocarditis, allergic encephalitis, gastritis, colitis; (immune)glomerulonephritis; pneumonia, toxic shock syndrome, viral infections, tuberculosis, hepatitis B, dengue fever, parasitic and helminthic MIF-related infections, in particular malaria, leishmaniasis, trypanosomiasis, toxoplasmosis, amoebiasis, schistosomiasis, cysticercosis, trichenellosis and filariasis; kidney diseases, like leukocyte-mediated renal injury, nonproliferative renal disease, proliferative renal disease, renal allograft rejection and congenital nephritic syndrome of the Finnish type, nephritis, nephropathy like uric acid nephropathies and hypertensive nephropathy, ureteric obstruction and diabetic nephropathy.

Neuropathic pain is a further MIF-related disease.

Most preferred diseases to be diagnosed according to the present invention are: glomerulonephritis, sepsis, lymphoma, lupus nephritis, psoriasis, ulcerative colitis and ophthalmological conditions, as well as Burkitt's lymphoma, leukemia, prostrate adenocarcinoma, pancreatic adenocarcinoma, and ovarian carcinoma.

One important aspect of the present invention is directed to detection of oxMIF in a sample of a subject; this detection will allow e.g. the skilled practitioner to determine whether or not MIF is a therapeutically important component of the disease or disorder which afflicts the subject in question. This determination will aid his decision whether or not an (additional) anti-(ox)MIF treatment could be beneficial for the subject in question.

OxMIF is also useful as a marker to determine a health or disease condition of a given subject in general; elevated oxMIF level will allow the finding that the subject is afflicted with a MIF related disease; oxMIF can thus also be used as a (secondary) general marker for a health/disease condition of a subject, similar e.g. to the determination of C-reactive protein (CRP) which is currently and widely used as such a (secondary) marker.

A subset of in vivo protective anti-oxMIF mAbs (e.g. RAB9, RAB4 and RAB0), which are directed against the pro-inflammatory cytokine oxMIF (Macrophage Migration Inhibitory Factor) do not bind to unmodified MIF in its reduced state (designated as redMIF). By contrast, these mAbs were shown to be highly selective for a redox dependent MIF isoform (designated as oxMIF). It was shown that oxMIF is not present in blood of healthy subjects and animals. It was also shown that oxMIF is not present on cellular surfaces of healthy subjects and animals. According to the present invention, and by the methods described herein, oxMIF can only be detected after onset of a disease. oxMIF was then (i.e. after onset of disease) shown to appear in the circulation or on the surface of cells. Stated differently: it was shown by the present inventors that oxMIF is clearly increased (i.e. detectable) in the circulation in samples of human or animal patients afflicted with a MIF related disease. It was also shown that oxMIF is strongly increased (and, thus, detectable) on the surface of cells afflicted with MIF related diseases. According to the present invention, detection of oxMIF in patients provides advantageous information regarding disease progression and therapeutic intervention. Therefore, oxMIF can be used as a diagnostic marker and the herein described methods will enable the monitoring of oxMIF during MIF-related diseases, e.g. affliction of a subject, e.g. a human, with inflammatory conditions or disease states like cancer.

Based on the described findings, the present invention is directed to the use of oxMIF as a marker in the diagnosis of MIF-related diseases. oxMIF is preferably MIF, which is differentially binding, as defined herein above, to antibody RAB9, RAB4 and/or RAB0. As explained above and shown in the experimental part, in particular the examples section, the present inventors showed for the first time that oxMIF is an isoform of MIF, which is encountered patient samples of MIF-related diseases, while it is not encountered, i.e. present as defined above, in normal healthy controls. Thus, oxMIF is most suitable as a marker in the diagnosis of MIF-related diseases. As it was shown by the present invention that oxMIF, in particular the amount thereof, is also correlated with the state of a disease and/or its progression; "diagnosis" in the context of this specification encompasses detection of a disease, evaluation of a disease state and monitoring of a disease progression, which also allows monitoring efficacy of a therapeutic treatment.

In a preferred embodiment, the diagnosis of said MIF-related diseases, which uses oxMIF as a marker, will encompass the further use of compounds binding to oxMIF for the detection of oxMIF.

These compounds, which differentially bind oxMIF can be antibodies or small molecules, which differentially bind to oxMIF.

The diagnostic assay which can be used in the present invention can be any diagnostic assay which is well-known to a person skilled in the art. In particular, the diagnostic assay can be carried out e.g. in an ELISA format, a sandwich (ELISA) format with use of FACS, immunofluorescence, immunohistochemistry, and all further suitable methods, all of which are well-known in the art.

The present invention will be in the following described by way of the examples, whereby the examples shall be considered by no means as limiting the present invention.

REFERENCE EXAMPLES

A) GCO-Assay for Antibody Screening

A THP1 suspension culture is centrifuged and cells are resuspended in fresh full medium to a cell density of $10^6$ cells per ml. This culture is transferred into wells of a 96-well microplate (90 µl/well) and a potential anti-MIF antibody is added to give a final concentration of 75 µg/ml. Each antibody is tested in triplicate. After o/n incubation at 37° C. dexamethasone is added to give a concentration of 2 nM and after one hour incubation at 37° C. LPS is added (3 ng/ml final concentration). After further six hours incubation at 37° C. the supernatant is harvested and the IL-6 concentrations are determined in a commercially available ELISA. The results of the triplicates are averaged and the percentage of IL-6 secretion is determined in comparison to the control antibodies. Antibodies that result in an IL-6 secretion of less than 75% are evaluated as positive.

B) Assay for Determination of $IC_{50}$ Values

The experimental procedure is carried out as described for the screening assay with the exception that increasing amounts of antibody are used (typically from 1-125 nM). The resultant dose response curve is expressed as % inhibition in comparison to a negative control antibody. This curve is used for calculation of the maximum inhibitory effect of the antibody (% Inh max) and the antibody concentration that shows 50% of the maximum inhibitory effect ($IC_{50}$).

C) Inhibition of Cell Proliferation

Serum stimulates secretion of MIF in quiescent NIH/3T3 and MIF in turn stimulates cell proliferation. Antibodies inhibiting this endogenous MIF, therefore, decrease the proliferation of quiescent NIH/3T3 cells. The reduction of proliferation is determined by the incorporation of $^3$H-thymidine.

1000 NIH/3T3 cells per well are incubated in a 96 well plate over the weekend at 37° C. in medium containing 10% serum. Cells are then starved over night at 37° C. by incubation in medium containing 0.5% serum. The 0.5% medium is removed and replaced by fresh medium containing 10% serum, 75 µg/ml antibody and 5µ Ci/ml of 3H-thymidine. After 16 hours incubation in a $CO_2$ incubator at 37° C. cells are washed twice with 150 µl of cold PBS per well. Using a multi-channel pipette 150 µl of a 5% (w/v) TCA solution per well are added and incubated for 30 minutes at 4° C. Plates are washed with 150 µl PBS. Per well 75 µl of a 0.5M NaOH solution with 0.5% SDS are added, mixed and stored at room temperature. Samples are measured in a β-counter by mixing 5 ml of Ultima Gold (Packard) and 75 µl sample solution. Each determination is done in triplicate and the values are compared with the values of the control antibody by a t-test. Antibodies that significantly reduce proliferation (P<0.05) are evaluated as positive.

D) Binding Studies: Epitope Determination of Anti-MIF Antibodies

Each peptide is diluted in coupling buffer to give a peptide concentration of typically 1/g/ml added to microplates (NUNC Immobilizer™ Amino Plate F96 Clear) and incubated over night at 4° C. (100 µl/well). As controls recombinant full length MIF and PBS are used. The plate is washed 3 times with 200 µl PEST and antibodies (2-4 µg/ml in PBS) are added (100 µl/well) and incubated for 2 hours at room temperature with gentle shaking. The plate is washed 3 times with 200 µl PEST and detection antibody (e.g. Fc specific anti-human IgG/HRP labeled, Sigma) is added (100 µl/well). After incubation for 1 hour at room temperature with gentle shaking, the plate is washed 3 times with 200 µl PEST. Each well is incubated with 100 µl TMB (3,3',5,5'-tetramethylbenzidine) solution (T-0440, Sigma) for 30 minutes in the dark. Staining reaction is stopped by adding 100 µl of 1.8 M $H_2SO_4$-solution per well. Samples are measured at 450 nm.

E) Affinity Determination of Fab Fragments of Anti-MIF Antibodies by Biacore Typically, 40 RU units of human recombinant MIF are immobilized on a sensor chip with a CM5 (=carboxymethylated dextran) matrix (Biacore). Fab fragments are injected at a concentration range of typically 6-100 nM diluted in HES-EP. After each cycle the chip is regenerated with 50 mM NaOH+1 M NaCl. Affinities are calculated according to the 1:1 Langmuir model.

EXAMPLES

The present examples relate to the finding that several specific antibodies only bind to oxMIF, but do not bind to unmodified MIF in a reduced state. This was shown by the detection of oxidized MIF by ELISA after mild oxidation of recombinant MIF by chemicals using a mock preparation, reduced MIF and untreated MIF as controls; this experiment was carried out in vitro and clearly showed that oxMIF was bound by specific antibodies, while control MIFs were not.

Anti-oxMIF antibodies RAB4, RAB9 and RAB0 were shown to be incapable of binding to MIF in its reduced state at physiologically relevant concentrations. In contrast, it was shown in vitro, that mild oxidation of MIF (e.g. with L-Cystine) can convert the MIF molecule into the antibody-binding isoform. Antibody-based screenings for oxMIF forms in vertebrate systems and cell lines (e.g. immortalized cell lines, plasma from mice, urine from rats, and plasma and urine from human donors) revealed, that the occurrence of such antibody-reactive MIF isoforms is linked to disease related processes (e.g. inflammation and neoplasia). This is why these antibodies can be used as tools for e.g. the diagnostic detection of native occurring disease-related oxMIF forms and for monitoring disease progression.

The present inventors have also shown for the first time that false positive results for oxMIF can be obtained. It is assumed that MIF protein can be converted to oxMIF by redox-active iron and heme in hemolytic blood samples and that MIF can be converted to oxMIF in biosamples, when oxidizing agents are added.

It is thus proposed according to a preferred embodiment for avoiding false positive results to avoid the addition of e.g. oxidizing agents and to de-activate redox-active iron and heme.

For example, a special sample procedure for the analysis of MIF circulating in blood is required. For the analysis of total and oxMIF, citrated plasma is preferred; to avoid false positive signals the samples in a preferred embodiment have to be prepared by the following steps:

Citrated plasma from fresh blood (stored at +4° C. not longer than 12 h) has to be centrifuged at 40 g for 5 min. The supernatant has to be transferred into a new tube and centrifuged again at 2000 g for 3 min. The cell free supernatant has to be transferred again into a new tube and centrifuged at 16000 g for 3 min. After the three centrifuge steps, the cell free supernatant can be stored at −80° C. or directly used for the analysis of (ox)MIF.

If sera should be analyzed regarding (ox)MIF, cells and insoluble fragments preferably have also to be removed by the same three centrifugation steps prior storage by freezing or prior running the MIF ELISA.

Sediments in urine samples also preferably have to be removed by a centrifugation step (16000 g for 5 min) prior to use in the MIF ELISAs. Generally, cells and other common particles occurring in biological fluids (e.g. tear fluid, saliva) have to be removed prior by a centrifugation step and then stored for testing of (ox)MIF.

Furthermore, the present inventors could show that MIF which is denatured is recognized by antibodies which specifically bind to oxMIF. Therefore, it is of utmost importance that for analysis of oxMIF, the MIF protein has to be kept in its native conformation during sample preparation (e.g. during the isolation and preparation of body fluids); therefore denaturating conditions/steps such as for example boiling, immobilization (on membranes, plastic (plate) or chips) and chemical treatments (e.g. with reducing agents, oxidizing agents and organic solvents), have to be avoided in order to keep the MIF protein in its native conformation and to avoid false positive/negative results during the analysis.

For analysis of oxMIF on cellular surfaces, preferably a flow cytometry assay is used. It is particularly important that the samples do not undergo hemolysis during sample preparation. Therefore, all samples for the present flow cytometry analysis have been prepared without any step which would lead to a hemolysis of the cells within the sample.

Example 1: Preparation of oxMIF Specific Antibodies (e.g. RAB0- or RAB4-Antibody)

The antibodies are produced in mammalian cells, preferentially in CHO cells, preferentially in CHO cells where the gene encoding for MIF (endogenous CHO-MIF) has been knocked out genetically. In the knock-out cells the contamination of the antibody with endogenous CHO-MIF can be abolished, which is desirable as sensitivity of the assays can be enhanced.

Typically, oxMIF specific antibodies were produced in a batch fermentation process using a disposal bioreactor (wave system) up to 25 L volume. Stable CHO cell lines harboring the genes encoding for the heavy and light chain of the produced antibody, respectively, were seeded into an PowerCHO medium (Invitrogen Inc.) and incubated at 37° C. and 5% $CO_2$.

In one exemplary production process, a CHO knock out cell line was used which comprised plasmids as deposited under DSM 25114 and DSM 25115.

During the cultivation, the respective human antibodies were continuously expressed into the cell culture medium. At the end of cultivation (viability<50%) the cells were separated by common centrifugation and filtration steps. The clarified cell culture supernatant (ccs) was concentrated by ultrafiltration and used for the purification of antibodies.

The human antibodies were purified from the concentrated ccs by Protein A affinity chromatography (MabSelect Sure, GE Healthcare). After equilibration of the Protein A material with 5 column-volumes (cv) of 20 mM sodium phosphate running buffer, pH 7 the concentrated supernatant of the isotype control was completely applied to the affinity column. Impurities or undesirable proteins were washed out with the running buffer. The antibodies were eluted by a pH shift using 100 mM glycine, pH 3 and dialyzed against 250 mM glycine buffer, pH 5.

Alternatively, the concentrated cell culture supernatant was applied to the Protein A column prior equilibrated with 5 cv of 20 mM Tris/HCl buffer including 150 mM sodium chloride buffer and 0.1% Tween 80, pH 7. Impurities were washed out by two washing steps: 1.) addition of 1 M NaCl in the equilibration buffer and 2.) 100 mM sodium phosphate including 0.1% Tween 80, pH 5. The RAB0 antibodies were eluted by 100 mM glycine buffer, pH 3 including 0.1% Tween 80 and then dialyzed against 250 mM glycine buffer, pH 5.

Example 2: Preparation of Polyclonal and Affinity Purified Polyclonal Rabbit Anti-Hu MIF Antibodies 1.) Production of Recombinant Human MIF (huMIF)

Recombinant huMIF was produced in *E. coli* cells including an expression system with the human MIF sequence. Fresh thaw cells were cultivated in Luria Bertani medium supplemented with Ampicillin (LB/Amp) over night at +37° C. At the next day, the bacterial cell culture was diluted with an equal volume of fresh LB/Amp medium and the expression induced by addition of IPTG (final concentration: 1.0 mM) at 30° C. for 4 hours. The bacterial pellet was harvested by centrifugation and stored at ≤−15° C.

For further purification of the intracellular human MIF proteins the frozen bacterial pellet was resuspended in 20 mM Tris/HCl buffer, pH 7.8 and cells were disrupted mechanically by glass beads. Cell debris was removed by centrifugation and filtration using a common 0.2 µm filter. The supernatant was directly applied to an anion exchange chromatography column (HiTrap 26/16 DEAE FF, GE Healthcare, Waukesha, USA) and MIF was purified by a passive binding mode. The flow through was rebuffered in 20 mM Bis/Tris pH 6.3 and further purified by a cation exchange chromatography (Source 30S, GE). Highly pure human MIF was eluted by a salt gradient of 50 mM NaCl in 20 mM Bis/Tris buffer, pH 6.3. Finally, the purified human MIF was rebuffered against PBS concentrated by ultrafiltration and characterized of purity and functionality.

2.) Immunization Procedure of Polyclonal Rabbit Anti huMIF Antibodies in New Zealand White Rabbits For the initial immunization, 25 µg of rec. human MIF diluted in 100 µl PBS was mixed with 100 µl CFA (Complete Freunds Adjuvants). 200 µl (4×50 41) of the mixture was applied s.c. to different body portions of each rabbit. After 2-3 weeks after the initial immunization a first boost with 25 µg of the rec. human MIF (suspended in 100 µl PBS) was mixed with 100 µl IFA (Incomplete Freunds Adjuvants). Again, 200 µl (4×50 µl) of the mixture was applied s.c. to different body portions of each rabbit. A second boost was performed 2-3 weeks after the first boost, 25 µg of the rec. human MIF (suspended in 100 µl PBS) was mixed with 100 µl IFA (Incomplete Freunds Adjuvants). Again, 200 µl (4×50 µl) of the mixture was applied s.c. to different body portions of each rabbit. The immunization procedure was terminated 2 weeks after the second boost. Typically, plasma from multiple rabbits was pooled and used for the isolation of the anti MIF antibodies.

3.) Protein a Purification and huMIF-Affinity Purification Procedure of Polyclonal Rabbit Anti huMIF Antibodies The isolation of rabbit anti huMIF antibodies from immunized plasma was typically done by two affinity chromatography steps. At first the plasma was purified by a Protein A affinity column (MabSelect Sure, GE Healthcare). To that avail, the rabbit plasma was diluted 1:3 with 20 mM $Na_2HPO_4$ buffer, pH 7.0 and applied to the affinity column. After a washing step (5 column volumes with 20 mM $Na_2HPO_4$ buffer, pH 7.0) the elution of total rabbit IgG was done with 100 mM glycine, pH 2.8. The eluate was pooled and neutralized to pH 7.0 using 1 M Tris/HCl. For hu-MIF affinity purification the total rabbit IgG was again diluted 1:3 with 20 mM $Na_2HPO_4$ buffer, PH 7.0 and applied to the 5 ml NHS-affinity column (GE Healthcare) coupled with 25 mg rhuMIF as recommended by the supplier. After a washing step (5 column volumes with 20 mM $Na_2HPO_4$ buffer, pH 7.0) the elution of the specific rabbit anti huMIF antibodies was effected with 100 mM glycine, pH 2.8. The eluate was pooled and neutralized to pH 7.0 using 1 M Tris/HCl. Finally, the hu-MIF affinity purified specific rabbit anti human MIF antibodies (in the following "anti-human Mid affinity purified polyclonal antibody") were dialyzed against PBS and stored at −20° C.

Example 3: Detection of oxMIF in Samples Obtained from Patients or from Animal Disease Models I. Sepsis Example 3.1: oxMIF in Plasma of *E. coli*-Challenged Mice We sought to look for systemic oxMIF forms in plasma samples of peritonitic mice that had been challenged with 2000 cfu (colony forming units) of the gram negative pathogenic *E. coli* strain O111:B4. Blood samples of healthy mice (treated with PBS) and diseased mice were taken 21 h after challenge and plasma has been analyzed for oxMIF.

Method

Microtiter plates were coated with anti oxMIF antibodies RAB0 or RAB4. MIF was detected with an affinity purified polyclonal rabbit anti-mouse MIF antibody and a commercial HRP conjugated goat anti rabbit IgG The antibodies were obtained similarly as described in Example 2, but in contrast to the Example 2 the rabbit anti moMIF antibodies were produced by rabbit immunization with recombinant moMIF and purified by affinity chromatography against Protein A and MIF (same procedures as described in Example 2). For quantification of reactive MIF from plasma samples, oxMIF standards are prepared by mixing untreated recombinant moMIF with a buffer (=ELISA dilution buffer) that contains 0.2% of the biocide Proclin300 (Sigma Aldrich). Proclin300 consists of oxidative isothiazolones that induce/conserve the binding oxMIF structure. All plates were developed with TMB (Sigma-Aldrich) and OD was measured in an ELISA reader after stopping the reaction with 3M $H_2SO_4$.

Results

FIG. 1A (FIG. 1B).

Analyses of plasma from seven different animal experiments have revealed considerable differences of total MIF and oxMIF levels. However, no oxMIF has ever been detected in plasma of PBS treated control mice (healthy controls), whereas oxMIF was almost always detected in plasma from septic mice. Range values from seven different experiments have been summarized in Table 1.

TABLE 1

Ranges of measured total MIF and oxMIF in mice (n = 7 expts.)

| | Total MIF [ng/ml] | oxMIF [ng/ml] |
|---|---|---|
| Control mice | 8-64 | n.d. |
| E. coli challenged mice | 2-112 | n.d.-36 |

Figure 1:
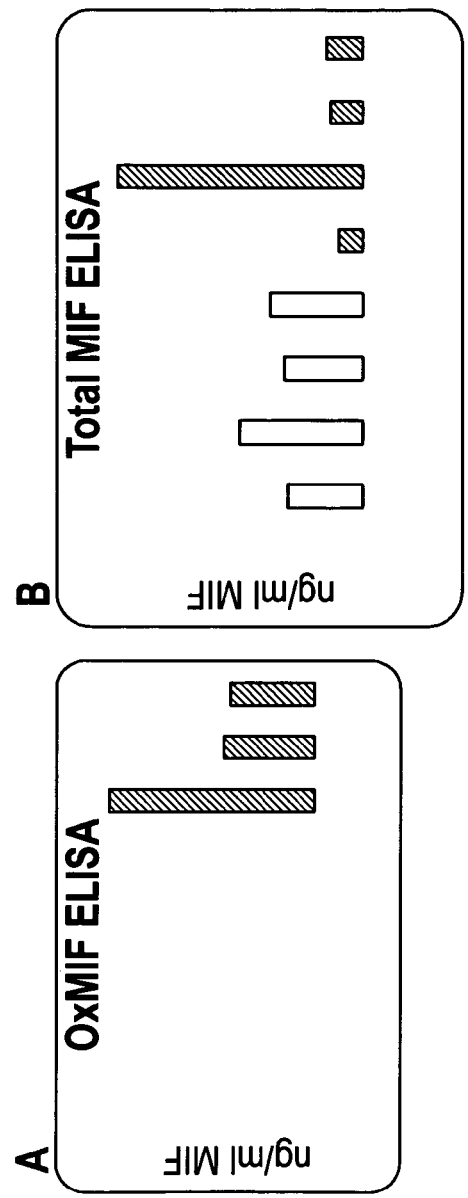
FIG. 1: TotalMiF and oxMIF in plasma of *E. coli* challenged mice

FIG. 1 shows one representative experiment in which oxMIF was detected only in septic mice with variations in oxMIF levels between mice (FIG. 1A). In this experiment total MIF level was elevated in the plasma of one mouse only and a significant portion of the total MIF in this mouse is oxMIF (FIGS. 1A and 1B, mouse E6), thus confirming that oxMIF is a better diagnostic marker for acute septicaemia than total MIF.

Conclusion

Total MIF is present in both healthy control mice and bacteriemic mice, but oxMIF levels correlate better to the stage of the disease than levels of total MIF.

Example 3.2: oxMIF on the Cellular Surface of Cells from E. coli-Challenged Mice Immune cells from peritonitic mice (or control mice injected with PBS only) have been analyzed for oxMIF by flow cytometry.

Methods

Blood from PBS- or E. coli-challenged mice was stained in Cell Staining Buffer (Biolegend) with either Alexa700-labeled anti-CD3ε (for T cells) and PerCP-Cy5.5-labeled anti-Ly6G (for granulocytes) or APC-labeled anti-CD14 (for monocytes) and PE-Cy7-labeled anti-CD19 (for B cells) in parallel with 300 nM RAB9 or control IgG. After washing, the human antibodies were detected using the goat R-PE-labeled anti-human IgG antibodies. After washing, the red blood cells were lysed with the BD FACS™ Lysing solution (Becton Dickinson, Franklin Lakes, USA). Data acquisition was performed using a FACS™ Canto II (Becton Dickinson) with the DIVA™ software (software version 6; Becton Dickinson) and the data were analyzed using the FlowJo™ software (Treestar, Ashland, Oreg., USA).

Results

The presence of oxMIF on the surface of the blood cells from peritonitic mice was analysed. Blood was harvested by cardiac puncture after 1, 3 or 21 h post-challenge, i.e. PBS for the control group and 2000 CFU E. coli for the peritonitic mice. The staining with RAB9 was performed on full blood and red cells were lysed before the analysis. FIG. 2 shows the histograms for the control mice (F) and challenged mice (E) at the different time points over a control IgG antibody (black line). In control mice, positive cells were not significantly detected with RAB9 for both, granulocytes-monocytes population and lymphocytes. oxMIF was not detected on the surface of lymphocytes but was present on the surface of both granulocytes (GR1 marker) and monocytes (CD14 marker), as soon as 1 h after challenge and up to 21 h.

Summary and Conclusion

In a peritonitis model in the mouse, we have been able to show the presence of oxMIF on the surface of granulocytes and monocytes during the time of infection and we have shown that oxMIF was not found in PBS-treated animals. These results demonstrate that oxMIF is a marker which appears in the course of an infection but is not present in healthy individuals.

Example 3.3: Detection of oxMIF in Sera of Bacteriemic Patients

Plasma samples from citrated blood were obtained from bacteriemic patients treated in intensive care unit (ICU) and have been analyzed for their content in MIF and oxMIF Material and Methods Both total MIF and oxMIF were detected using the same ELISA set up: microtiter plates were coated with the human anti-MIF monoclonal antibody RAB0 and detection was done with an affinity purified polyclonal rabbit antibody anti-human MIF. Finally, the read-out of the ELISA was done after incubation of goat anti-rabbit, HRP conjugated (BioRad, Cat.: 171-6516) (any other goat anti-rabbit as known in the art could be used here as well) and TMB substrate (a chromogenic substrate, as defined above; any other suitable substrate could also be used, as known to a person skilled in the art) at 450 nm. The calibration of the ELISA was done with a recombinant human oxMIF which was freshly produced by an oxidation step of redMIF by adding of 0.2% ProClin300. The standards were diluted in 0.5% fish gelatin/PBS including 0.2% ProClin300 and 4% human control plasma. The range of the calibration curve is 10 ng/ml to 0.156 ng/ml. The tested human serum samples were diluted 1:25 in 0.5% fish gelatin/PBS, pH 7.2 for oxMIF ELISA, or in the presence of Proclin300 for the total MIF ELISA in order to transform every reduced MIF molecules present in the plasma in oxMIF.

Results

Plasma samples from citrated blood have been obtained from patients treated in an ICU for septicaemia (n=6). Gender, age, infectious germs and treatments are all different. FIG. 3 shows the levels of total MIF and oxMIF detected in the plasma of the patients as well as in one healthy donor or from a pool of 50 plasma samples from healthy donors. Total MIF is present in every sample but oxMIF is detected only in 2 out of 6 bacteremic patients.

Conclusion oxMIF can be detected in the plasma of some of the bacteremic patients tested (2 out of 6), but not in the plasma of healthy donors. OxMIF can be used as a marker for septicaemia.

II. Psoriasis

Example 3.4: Detection of oxMIF in Sera of Psoriasis Patients

Sera samples collected from psoriatic patients have been analyzed for their content in oxMIF. The sera were taken from patients with systemic anti-psoriatic therapy at different time points (start, 12 weeks and 24 weeks).

Material and Methods
Measurement of oxMIF in Serum by a Sandwich ELISA:

Microtiter plates were coated with the monoclonal fully human anti-oxMIF antibody RAB0. The human serum samples were diluted 1:25 in 0.5% fish gelatin/PBS, pH 7.2. The calibration of the ELISA was done with a recombinant human oxMIF which was freshly produced by adding of 0.2% ProClin300. The standards were diluted in 0.5% fish gelatin/PBS including 0.2% ProClin300 and 4% human control plasma (i.e. a pool of serum samples from 50 healthy donors). The range of the calibration curve was 10 ng/ml to 0.156 ng/ml. After washing of the plate, oxMIF captured by the coating antibody was detected by an affinity purified polyclonal rabbit anti-human MIF antibody (rabbit anti-huMIF, does not distinguish between redMIF and oxMIF) and HRP labelled goat anti-rabbit antibodies. TMB was used as chromogenic substrate, chromogenic reaction was stopped with $H_2SO_4$ and the ELISA plate was measured at 450 nm. All samples, standards and controls, were done in duplicate.

Results

We were able to detect increased levels of oxMIF in serum of patients with psoriasis. During treatment with systemic immunomodulators levels of oxMIF decreased correlating with an improvement of the patient's condition (FIG. 4).

Conclusion oxMIF levels have been detected in serum samples of psoriatic patients. This means that oxMIF is very sensitive in chronic or acute inflammatory skin diseases like psoriasis and can also be used as a marker for the severity of the disease and to monitor disease development during systemic anti-psoriatic therapy.

III. Nephritis

Example 3.5: oxMIF in the Urine of Rats after Establishment of Proliferative Glomerulonephritis Material and Methods
Rat Model for Proliferative Glomerulonephritis:

OxMIF levels were analyzed in urine of Wistar Kyoto (WKY) rats after induction of proliferative glomerulonephritis by application of a single intravenous injection of rabbit anti-rat glomerular basement membrane serum (=nephrotoxic serum, NTS) (Tam FWK, Nephrol Dial Transplant, 1999, 1658-1666). The urine samples were collected using metabolic cages before induction of the disease. Four and six days after induction of disease rats were treated with a human control antibody, or different doses of the human anti-oxMIF antibody RAB9. The second urine sampling was done before sacrificing the animals on day 8 for histological evaluation. OxMIF levels measured in the urine were correlated with other disease parameters like proteinuria or histology data of the kidney (crescent formation and macrophage infiltration).

Measurement of oxMIF in Urine by a Sandwich ELISA

Microtiter plates were coated with the monoclonal fully human anti-oxMIF antibody RAB0. The urine samples were diluted 1:10 in 2% BSA/TBST pH 7.2. For the standard calibration curve, recombinant moMIF protein was modified by adding 0.2% ProClin300 and the standards were diluted in 2% BSA/TBST including 0.2% ProClin300. Detection was achieved by an affinity purified polyclonal anti-mouse MIF antibody (rabbit anti-moMIF, as described in Example 3.1) and a HRP-conjugated goat anti-rabbit antibodies. TMB was used as chromogenic substrate, chromogenic reaction was stopped with $H_2SO_4$ and the ELISA plate was measured at 450 nm. All samples, standards and controls, were done in duplicate.

Results

Before disease induction the mean level of oxMIF was not significantly above 0. Four days after disease induction significant levels of oxMIF became detectable. During disease progression the urinary oxMIF levels increased in the untreated control group on day 8 up to 333 ng/day (mean 130 ng/day). On day 8 the mean level of oxMIF in the anti-MIF antibody treated group was by approx. 70% decreased in comparison to the non treated group (see FIG. 5A). The reduced level of oxMIF in the treated group correlated with reduced disease parameters such as proteinuria and macrophage infiltration (FIG. 5B).

Conclusion

The level of oxMIF in urine correlates with the disease state in an animal model for proliferative glomerulonephritis. After administration of anti-oxMIF antibody RAB0, oxMIF levels were significantly reduced. Therefore, we conclude that measurement of oxMIF is suitable as a diagnostic marker to monitor disease progression and treatment effectiveness of Nephritis.

Example 3.6: oxMIF in Urine and Plasma of Lupus Nephritis Patients

Urine and plasma samples were collected from Lupus Nephritis patients at different stages of disease. Each sample was stored frozen at −20° C. and shipped on dry ice.

Material and Methods
Preparation of oxMIF Specific Antibodies:

The same antibody preparations were used as described in Example 1.

Measurement of oxMIF in Urine by a Sandwich ELISA:

Microtiter plates were coated with the monoclonal fully human anti-oxMIF antibody RAB0. The human urine samples were diluted 1:10 in 0.5% fish gelatine/PBS, pH 7.2. The calibration of the ELISA was done with a recombinant human oxMIF which was freshly produced by adding of 0.2% ProClin300. The standards were diluted in 0.5% fish gelatin/PBS including 0.2% ProClin300 and 10% human control urine (i.e. a pool of urine samples from >10 healthy donors). After washing of the plate, oxMIF captured by the coating antibody was detected by an affinity purified polyclonal rabbit anti-human MIF antibody (rabbit anti-huMIF, does not distinguish between redMIF and oxMIF) and HRP labelled goat anti-rabbit antibodies. TMB was used as chromogenic substrate, chromogenic reaction was stopped with $H_2SO_4$ and the ELISA plate was measured at 450 nm. All samples, standards and controls, were done in duplicate.

Measurement of oxMIF in Plasma by a Sandwich ELISA:

Microtiter plates were coated with the monoclonal fully human anti-oxMIF antibody RAB0. The human plasma samples were diluted 1:20 in 0.5% fish gelatin/PBS, pH 7.2. The calibration of the ELISA was done with a recombinant human oxMIF which was freshly produced by adding of 0.2% ProClin300. The standards were diluted in 0.5% fish gelatine/PBS including 0.2% ProClin300 and 5% human control plasma (i.e. a pool of plasma samples from 150 healthy donors). The range of the calibration curve was 10 ng/ml to 0.156 ng/ml. After washing of the plate, oxMIF captured by the coating antibody was detected by an affinity purified polyclonal rabbit anti-human MIF antibody (rabbit anti-huMIF, does not distinguish between redMIF and oxMIF) and HRP labelled goat anti-rabbit antibodies. TMB was used as chromogenic substrate, chromogenic reaction was stopped with $H_2SO_4$ and the ELISA plate was measured at 450 nm. All samples, standards and controls, were done in duplicate.
Results The data depicted in FIG. 6A show a clear correlation between the amount of oxMIF detected in the urine and the state (stage) of the disease. The mean level of oxMIF determined in the urine of healthy controls was not significantly above 0. However, the more severe the disease state, the higher the mean oxMIF concentration determined in the urine.

Figure 6C:
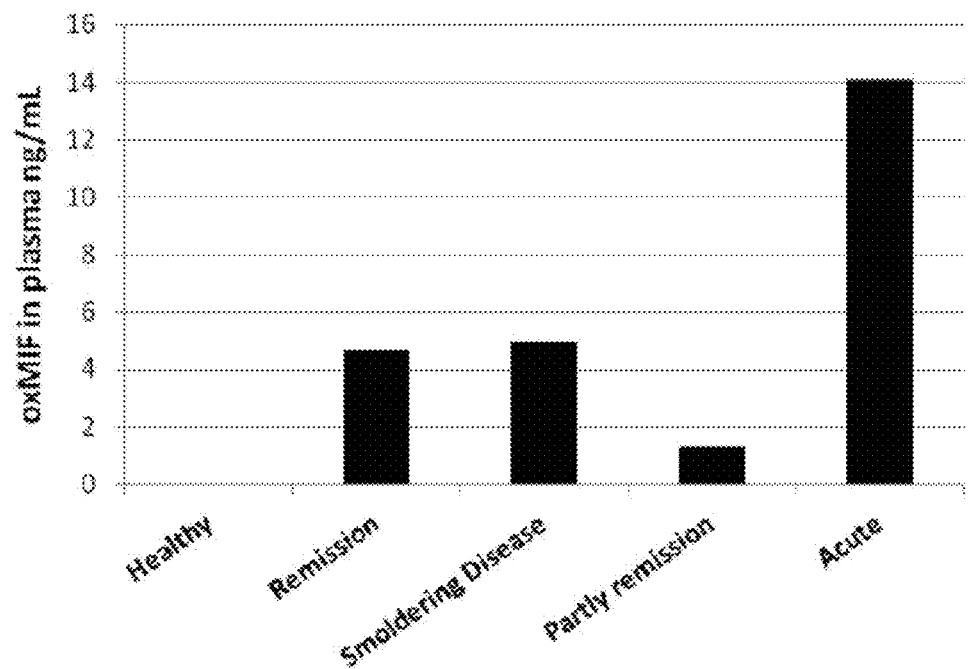

OxMIF levels of an acute patient diagnosed with Lupus Nephritis was measured at first observation day, 9 days and 35 days post diagnosis. Constant reduction in oxMIF levels correlated with improved clinical symptoms (FIG. 63). OxMIF levels in plasma were also measured and the results were comparable to the urinary levels. However, correlation with partly remission, remission or smoldering disease were less pronounced most probably because oxMIF in the circulation reflects overall the activity of the underlying disease (SLE) and not only the situation in the kidney (FIG. 6C).
Conclusion Measurement of oxMIF in urine of lupus nephritis patients is suitable to monitor for disease progression as well as treatment efficiency. OxMIF in the circulation also correlates with disease severity although the result probably reflects the overall situation of the patients regarding SLE and not only the situation in the kidney (LN).

IV. Diabetic Retinopathy

Example 3.7

Aqueous humor samples taken from patients with diabetic retinopathy (DR) and cataract as controls were assayed for the presence of MIF and oxMIF by ELISA.
Material and Methods Total MIF and oxMIF were detected with the same ELISA set up described in examples 3.3 and 3.4.
Results As shown on FIG. 7, total MIF is detected in the samples from DR or cataract patients, but oxMIF is only detected in DR samples.
Conclusion OxMIF can be used as a marker in diabetic retinopathy.

V. Prostate Cancer

Example 3.8: OxMIF in Mouse Plasma after Establishment of a Human Prostate Cancer Plasma samples were collected at the time of termination of a xenograft mouse prostate cancer model. oxMIF as well as total MIF levels were measured and correlated with tumor growth in isotype control and anti-MIF treated mice.
Material and Methods
Xenograft Model for Prostate Cancer.

Figure 8B:
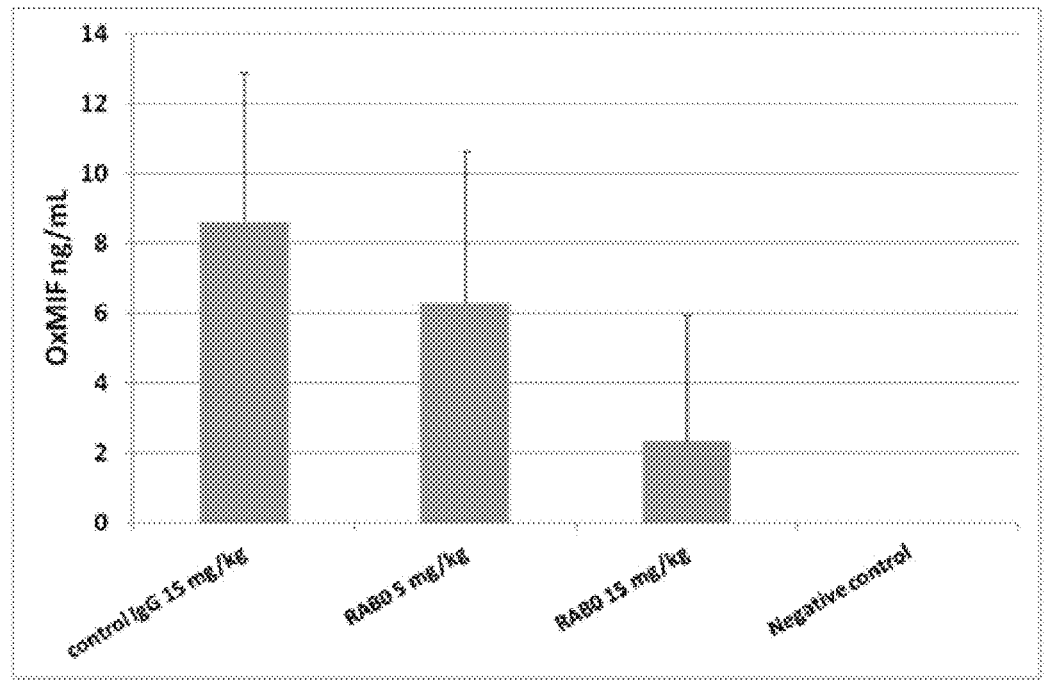
Figure 8C:
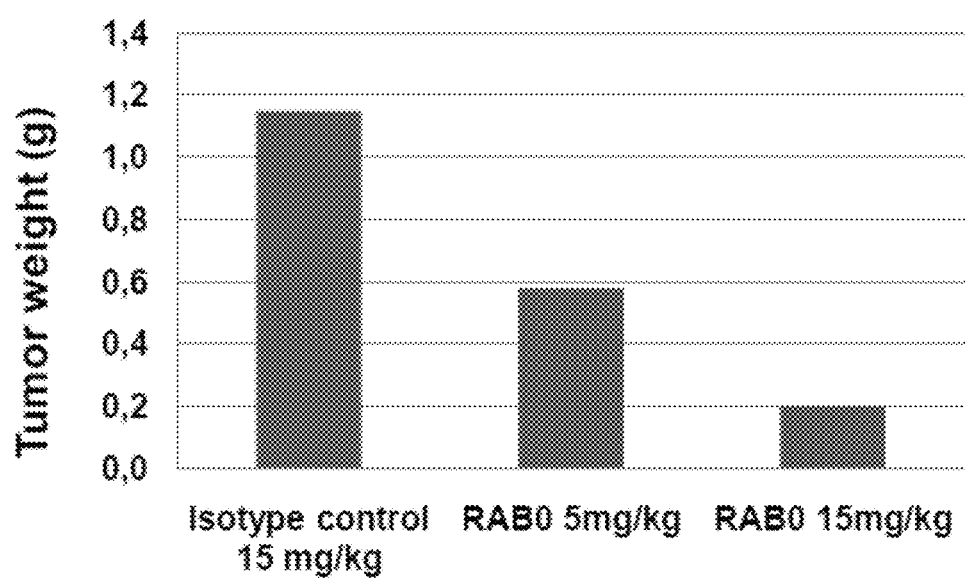

PC-3 cells were harvested from exponentially growing cultures and mixed with growth factor-depleted BD matrigel matrix. The suspension was inoculated subcutaneously into the right flank of MF1 nude mice ($2 \times 10^6$ cells in 250 µl matrigel per mice, 10 mice per group). One day after tumour induction, antibody treatment with RAB0 was started (5 and 15 mg/kg) and the antibodies were injected i.p. every second day for 2 weeks. Blood was collected by heart puncture and plasma was prepared for measurement the day of circulating MIF levels. Plasma samples from non-xenografted mice were also analyzed for total MIF and oxMIF (=negative control). In addition, tumour weight was measured.
Measurement of Total MIF in Plasma by a Sandwich ELISA:

Microtiter plates were coated with an affinity purified polyclonal rabbit anti-mouse MIF antibody (rabbit anti-moMIF, as described in Example 2). The tested plasma samples were diluted 1:25 in 0.5% fish gelatin/PBS, pH 7.2. The calibration of this ELISA was done by a recombinant full length mouse MIF protein. The standards were diluted in 0.5% fish gelatin/PBS including 4% control plasma. Detection of captured MIF was achieved by an affinity purified and biotinylated polyclonal rabbit anti-mouse MIF antibody (biot. rabbit anti-moMIF). All samples, standard and controls were done in duplicates
Measurement of oxMIF in Plasma by a Sandwich ELISA:

Microtiter plates were coated with the monoclonal fully human anti-oxMIF antibody RAB0. The plasma samples were diluted 1:25 in 2% BSA/TEST pH 7.2. For the standard calibration curve, recombinant moMIF protein was modified by adding 0.2% ProClin300 and the standards were diluted in 2% BSA/TEST including 0.2% ProClin300 and 4% control plasma. Detection of captured oxMIF was achieved by an affinity purified polyclonal anti-mouse MIF antibody (rabbit anti-moMIF, as described in Example 3.1) and a HRP-conjugated goat anti-rabbit antibodies. TMB was used as chromogenic substrate, chromogenic reaction was stopped with $H_2SO_4$ and the ELISA plate was measured at 450 nm. All samples, standards and controls, were done in duplicate.
Results The median of total MIF in the isotype control treated group did not differ significantly from the anti-MIF antibody treated animals. Levels of total MIF were found to be increased in tumour bearing animals when compared to non-xenografted mice (=negative control in FIG. 8A). However, oxMIF levels in healthy animals are not detectable by the methods applied (=negative control in FIG. 8B; see also example 3.8). But as depicted in FIG. 8B, oxMIF levels were clearly detectable in tumor bearing mice. In addition, oxMIF levels were significantly reduced after treatment with an anti-MIF antibody. The median oxMIF level in the control group was found to be 8.6 ng/mL and was reduced in the two treatment groups. The dose dependent reduction of oxMIF levels also correlated with the reduction in tumor growth, thus with the therapeutic effect achieved (FIG. 8C).
Conclusion In the PC-3 prostate cancer xenograft model, levels of total MIF were found to be increased in tumor bearing mice. However, oxMIF is not detected in non-xenografted control mice and concentration of oxMIF, but not of total MIF, correlates with tumor growth in MF1 nude mice. OxMIF is therefore much more suitable as a diagnostic marker for monitoring disease progression and therapeutic effects than total MIF.

Example 3.9: oxMIF on the Cellular Surface of a Prostate Cancer Cell Line

The human prostate cancer cell line PC-3 (prostate adenocarcinoma, ATCC® CRL-1435') has been tested by flow cytometry for the expression of oxMIF on its surface.
Methods Cells were stained in Cell Staining 'Buffer (Biolegend) with 300 nM antibody RAB9 or RAB0 and "Control 1", (irrelevant isotype control antibody) as the negative control, and antibodies were detected with the R-PE anti-human IgG (Sigma).

Human blood from healthy donors was also analyzed to assess the presence of oxMIF on the surface of leukocytes in a "normal" situation. Heparinized blood was first incubated with anti-human Fc Receptors (anti-CD16, anti-CD32 and anti-CD64) to block unspecific binding of the antibody through their Fc domain to the cells. Cells were then incubated with a control IgG1 human monoclonal antibody, with RAB9 or with RAB0. Detection of cell surface bound antibodies was done with an R-PE-labelled rabbit anti-human IgG. In order to differentiate the different leukocyte subpopulations, cells were also labelled with a Pacific Blue-labelled anti-CD45 (pan-leukocyte marker) and an APC-labelled anti-CD19 (B cell marker). Acquisition is done after lysing the red blood cells. Using the size and complexity parameters as well as the CD19 staining, we are able to distinguish between the granulocytes, monocytes, lymphocyte B cells (CD19+ cells) and lymphocyte T cells+Natural Killer cells (CD19neg cells). The acquisition of the data was carried out with a FACS™ CANTO II (Becton Dickinson) and data were analyzed with the FlowJo software (Treestar).

Results oxMIF can be found on the surface of human prostate cancer cell line PC-3 (FIG. 9). Leukocytes from healthy donors (neg. control) do not show any oxMIF on their cell surface (FIG. 10).

Conclusion

The presence of oxMIF on the surface of human prostate cancer cells shows that oxMIF can be used as a marker for detection of cancerous cells.

VI. Pancreatic Cancer

Example 3.10: oxMIF on the Cellular Surface of Pancreatic Cancer Cell Line

The human pancreatic cancer cell line BxPC-3 (Human primary pancreatic adenocarcinoma, Health Protection Agency (HPA) #93120816) has been tested by flow cytometry for the expression of oxMIF on its surface.

Methods

Cells were stained in Cell Staining 'Buffer (Biolegend) with 300 nM antibody RAB9 or RAB0 and "Control 1" (irrelevant isotype control antibody), as the negative control, and antibodies were detected with the R-PE anti-human IgG (Sigma). The acquisition of the data was carried out with a FACS™ CANTO II (Becton Dickinson) and data were analyzed with the FlowJo software (Treestar).

Results oxMIF can be found on the surface of human pancreatic cancer cell line BxPC-3 (FIG. 11). Leukocytes from healthy donors (neg. control) do not show any oxMIF on their cell surfaces (FIG. 10).

Conclusion

The presence of oxMIF on the surface of human pancreatic cancer cells shows that oxMIF can be used as a marker for detection of cancerous cells.

VII. Ovarian Cancer

Example 3.11: oxMIF on the Cellular Surface of Ovarian Cancer Cell Line

The human ovarian cancer cell line A2780 (Human ovarian carcinoma, HPA #93112519) has been tested by flow cytometry for the expression of oxMIF on its surface.

Methods

Cells were stained in Cell Staining 'Buffer (Biolegend) with 300 nM antibody RAB9 or RAB0 and "Control 1" (irrelevant isotype control antibody), as the negative control, and antibodies were detected with the R-PE anti-human IgG (Sigma). The acquisition of the data was carried out with a FACS™ CANTO II (Becton Dickinson) and data were analyzed with the FlowJo software (Treestar).

Results oxMIF can be found on the surface of human ovarian cancer cell line A2780 (FIG. 12), but mainly with the monoclonal antibody RAB0. Leukocytes from healthy donors (neg. control) do not show any oxMIF on their cell surfaces (FIG. 10).

Conclusion

The presence of oxMIF on the surface of human ovarian cancer cells shows that oxMIF can be used as a marker for detection of cancerous cells.

VIII. Lymphoma

Example 3.12: oxMIF on the Cellular Surface of Lymphoma Cancer Cell Line

Different immortalized human lymphoma cell lines (Table 2) have been tested by flow cytometry for the expression of oxMIF on their surfaces.

TABLE 2

| Cell lines that have been positively tested for active MIF by flow cytometry | | |
|---|---|---|
| Name | Reference | Origin |
| CA46 | ATCC ® CRL-1648 ™ | Burkitt's Lymphoma |
| MC/CAR | ATCC ® CRL-8083 ™ | B lymphocyte, plasmacytoma myeloma |
| Raji | ATCC ® CCL-86 ™ | Burkitt's Lymphoma |
| U-937 | ATCC ® CRL-1593.2 ™ | Histiocytic Lymphoma |

Methods

Cells have been stimulated (or not) with 25 µg/ml LPS and 50 µg/ml Dextran sulfate for 24 h up to 72 h. Cells were stained in Cell Staining 'Buffer (Biolegend) with 300 nM antibody RAB9 or RAB0 or RAB4 and "Control 1" (irrelevant isotype control antibody), as the negative control, and antibodies were detected with the R-PE anti-human IgG (Sigma). The acquisition of the data was carried out with a FACS™ CANTO II (Becton Dickinson) and data were analyzed with the FlowJo software (Treestar).

Results oxMIF can be found on the surface of human lymphoma cell lines (FIG. 13), whereas leukocytes from healthy donors (neg. control) do not show any oxMIF on their cell surfaces (FIG. 10).

Conclusion

The presence of oxMIF on the surface of human lymphoma cells shows that oxMIF can be used as a marker for detection of cancerous cells.

IX. Solid Tumour

Prostate and Breast Cancer

Example 3.13: oxMIF in the Plasma from Cancer Patients

EDTA plasma samples from patients having different kinds of solid tumors (prostate and breast) were obtained from a commercial vendor. The total MIF and oxMIF concentrations were analyzed by sandwich ELISA.
Material and Methods Both total MIF and oxMIF were detected using the same ELISA set up: microtiter plates were coated with human anti-MIF monoclonal antibody RAM0 and detection of MIF was done with an affinity purified, polyclonal rabbit anti-human MIF antibody. The read-out of the ELISA was done after incubation of the plate with an goat anti-rabbit, HRP conjugated antibody (BioRad, Cat.: 171-6516) (any other goat anti-rabbit could be used here as well) and TMB (chromogenic substrate; any other suitable chromogenic substrate could also be used, as known to a person skilled in the art) in an ELISA reader at 450 nm. The calibration of the ELISA was done with recombinant human MIF which was incubated with 0.2% ProClin300 (Proclin300 induces the formation of oxMIF epitopes within MIF). The standards were diluted in 0.5% fish gelatin/PBS including 0.2% ProClin300 and 5% human control plasma. The range of the calibration curve was 10 ng/ml to 0.156 ng/ml. The tested human plasma samples were diluted 1:20 either in 0.5% fish gelatin/PBS, pH 7.2 for the oxMIF ELISA, or in 0.5% fish gelatin/PBS/0.2% Proclin300 for the total MIF ELISA.
Results EDTA plasma samples derived from patients diagnosed with prostate cancer (n=14) and breast cancer (n=15) have been purchased from a commercial vendor. EDTA plasma from healthy volunteers (n=49) was used as control. In FIGS. 14A and 14B levels of total MIF and oxMIF of control samples and prostate cancer samples are shown. As described in the literature, MIF was detected in the plasma from healthy individuals and a significant increase of total MIF in the plasma from prostate cancer patients (t test, p=0.0166) was observed. However, oxMIF was not detected in the plasma of healthy donors, whereas oxMIF was detected in the plasma samples from the prostate cancer patients (t test, n=0.0016). A similar pattern was observed in breast cancer samples (FIG. 15) with a significant elevation of total MIF (p=0.0078) and oxMIF (p=0.0451) in the plasma samples derived from breast cancer patients compared to the healthy controls and no oxMIF detection in healthy controls.
Conclusion Elevated levels of total MIF and oxMIF can be detected in the plasma of patients with prostate and breast cancer. However, total MIF is also present in the plasma derived from healthy donors, whereas oxMIF cannot be detected in healthy controls. Therefore, oxMIF can be considered as a more specific biomarker to indicate a disease state than total MIF.

X. Multiple Sclerosis

Example 3.14: oxMIF in the CSF of Multiple Sclerosis Patients

Cerebrospinal fluid samples derived from patients with different forms of multiple sclerosis were obtained from a commercial vendor. The total MIF and oxMIF concentrations were measured by sandwich ELISA.
Material and Methods Both total MIF and oxMIF were detected using the same ELISA set up: microtiter plates were coated with human anti-MIF monoclonal antibody RAM0 and detection of MIF was done with an affinity purified polyclonal rabbit anti-human MIF antibody. The read-out of the ELISA was done after incubation of the plate with an goat anti-rabbit, HRP conjugated antibody (BioRad, Cat.: 171-6516) (any other goat anti-rabbit could be used here as well) and TMB (chromogenic substrate, as defined above; any other suitable chromogenic substrate could also be used, as known to a person skilled in the art) in an ELISA reader at 450 nm.

For the CSF samples, the calibration of the ELISA was done with recombinant human MIF which was incubated with 0.2% ProClin300 (Proclin300 induces the formation of oxMIF epitopes within MIF). The standards were diluted in 20 mM Tris/TBST buffer pH 7.2 including 0.2% ProClin300. The range of the calibration curve is 10 ng/ml to 0.156 ng/ml. The tested human CSF samples were diluted 1:10 in 20 mM Tris/TEST, for the oxMIF ELISA, or in the presence of Proclin300 for the total MIF ELISA.
Results In the cerebrospinal fluid (CSF) samples as used in this example (FIGS. 16 A and 16B), oxMIF was not detectable in the CSF from healthy controls, whereas high levels were found in the CSF of MS patients ($p<0.0001$). Also the levels of total MIF were strongly increased in samples from MS patients (n=49) as compared to the controls (n=30) ($p<0.0001$), but to a certain extent, total MIF was also found in samples from healthy controls.
Conclusion Elevated levels of total MIF and oxMIF can be detected in the CSF of MS patients. However, total MIF is also present in the CSF derived from healthy donors, whereas oxMIF cannot be detected in healthy controls. Therefore, oxMIF can be considered as an excellent biomarker for multiple sclerosis and as a more specific biomarker than total MIF.

XI. Ovarian Cancer

Example 3.15: oxMIF in the Plasma from Ovarian Cancer Patients

EDTA plasma samples were commercially obtained from patients having different kind of ovarian cancers (clear cell adenocarcinoma, papillary serous adenocarcinoma and serous adenocarcinoma). Their content in total MIF and oxMIF was analyzed by sandwich ELISA.
Material and Methods Both total MIF and oxMIF were detected using the same ELISA set up: microtiter plates were coated with human anti-MIF monoclonal antibody RAM0 and detection of MIF was done with an affinity purified polyclonal rabbit anti-human MIF antibody. The read-out of the ELISA was done after incubation of the plate with an goat anti-rabbit, HRP conjugated antibody (BioRad, Cat.: 171-6516) (any other goat anti-rabbit as known in the art could be used here as well) and TMB (chromogenic substrate, as defined above; any other suitable chromogenic substrate could also be used, as known to a person skilled in the art) in an ELISA reader at 450 nm. The calibration of the ELISA was done with recombinant human MIF which was incubated with 0.2% ProClin300 (Proclin300 converts MIF to oxMIF). The standards were diluted in 0.5% fish gelatin/PBS including 0.2% ProClin300 and 5% human control plasma. The range of the calibration curve is 10 ng/ml to 0.156 ng/ml. The tested human plasma samples were diluted 1:20 in 0.5% fish gelatin/PBS, pH 7.2 for the oxMIF ELISA, or in the presence of Proclin300 for the total MIF ELISA.
Results Plasma samples from EDTA blood have been purchased from patients diagnosed with ovarian cancer (n=42). EDTA plasma from healthy volunteers (n=19) was used as control.

In FIGS. 17A and 17B levels of total MIF and oxMIF of control samples and ovarian cancer samples are shown. As described in the literature, MIF was detected in the plasma from healthy individuals and a significant increase of total MIF in the plasma from ovarian cancer patients (t test, p=0.0434) was observed. However, no oxMIF was detected in the plasma of healthy donors, whereas oxMIF was detected in the plasma samples from the ovarian cancer patients (t test, p=0.0663). When the statistical analysis is run on specific subtypes of ovarian cancer, a significant increase of MIF in plasma from serous cystadenocarcinoma over the controls (p=0.0046), as well as a significant increase of oxMIF in papillary serous cystadenocarcinoma (p=0.0438) and serous cystadenocarcinoma (p=0.0357) over the controls was observed.

XII: Ulcerative Colitis and Crohn'S Disease

Example 3.16: oxMIF in the Plasma from Patients with Ulcerative Colitis and Crohn's Disease EDTA plasma samples were commercially obtained from patients having different ulcerative colitis (UC) or Crohn's Disease (CD). Their content in total MIF and oxMIF was analyzed by sandwich ELISA.

Material and Methods

Both total MIF and oxMIF were detected using the same ELISA set up: microtiter plates were coated with human anti-MIF monoclonal antibody RAM0 and detection of MIF was done with an affinity purified polyclonal rabbit anti-human MIF antibody. The read-out of the ELISA was done after incubation of the plate with an goat anti-rabbit, HRP conjugated antibody (BioRad, Cat.: 171-6516) (any other goat anti-rabbit as known in the art could be used here as well) and TMB (chromogenic substrate, as defined above; any other suitable chromogenic substrate could also be used, as known to a person skilled in the art) in an ELISA reader at 450 nm. The calibration of the ELISA was done with recombinant human MIF which was incubated with 0.2% ProClin300 (Proclin300 converts MIF to oxMIF). The standards were diluted in 0.5% fish gelatin/PBS including 0.2% ProClin300 and 5% human control plasma. The range of the calibration curve is 10 ng/ml to 0.156 ng/ml. The tested human plasma samples were diluted 1:20 in 0.5% fish gelatin/PBS, pH 7.2 for the oxMIF ELISA, or in the presence of Proclin300 for the total MIF ELISA.

Results

Plasma samples from EDTA blood have been purchased from patients diagnosed with UC (n=15) or CD (n=21). EDTA plasma from healthy volunteers (n=19) was used as control. In FIGS. 18A and 18B levels of total MIF and oxMIF of control samples and UC and CD samples are shown. As described in the literature, MIF was detected in the plasma from healthy individuals and a significant increase of total MIF was detected in the plasma from CD patients (t test, p=0.0207), but not in UC samples (p=0.1240). However, no oxMIF was detected in the plasma of healthy donors, whereas oxMIF was detected in the plasma samples from both UC and CD patients (t test, p=0.0417 and p=0.0114, respectively when compared to controls).

Conclusion

For both ulcerative colitis and Crohn's disease patients, it was possible to detect a significant higher amount of oxMIF in the plasma as compared to healthy volunteers. These results show that oxMIF can be used as a biomarker in these diseases

The invention claimed is:

1. A method for in vitro diagnosis of a disease related to the presence of oxMIF in a subject, said method comprising:
   a) contacting a sample from said subject with an anti-oxMIF antibody wherein said antibody binds oxMIF but not redMIF;
   wherein said antibody is selected from the group consisting of:
   i. a RAB4 antibody, characterized by a light chain sequence as deposited by way of plasmid deposition with deposit number DSM 25110 and a heavy chain sequence as deposited by way of plasmid deposition with deposit number DSM 25112,
   ii. a RAB9 antibody, characterized by a light chain sequence as deposited by way of plasmid deposition with deposit number DSM 25111 and a heavy chain sequence as deposited by way of plasmid deposition with deposit number DSM 25113,
   iii. a RAB0 antibody, characterized by a light chain sequence as deposited by way of plasmid deposition with deposit number DSM 25114 and a heavy chain sequence as deposited by way of plasmid deposition with deposit number DSM 25115,
   iv. a RAB4 antibody, which is characterized by a light chain amino acid sequence of SEQ ID NO: 2 and a heavy chain amino acid sequence of SEQ ID NO:6,
   v. a RAB9 antibody, which is characterized by a light chain amino acid sequence of SEQ ID NO: 1 and a heavy chain amino acid sequence of SEQ ID NO:5,
   vi. a RAB0 antibody, which is characterized by a light chain amino acid sequence of SEQ ID NO: 3 and a heavy chain amino acid sequence of SEQ ID NO:7, and
   b) detecting the presence of oxMIF in said sample by detecting the binding of said anti-oxMIF antibody to said sample, wherein binding of said anti-oxMIF antibody to said sample is indicative of the presence of oxMIF in said sample, and wherein the presence of a higher level of oxMIF in said sample as compared to the level of oxMIF in a healthy control is indicative of the presence of a MIF-related disease in said sample.

2. The method according to claim 1, wherein said sample is a body fluid sample of said subject.

3. The method according to claim 1, wherein said sample is a cellular sample of said subject.

4. The method of claim 1 wherein said antibody is a RAB4 antibody, which is characterized by a light chain amino acid sequence of SEQ ID NO: 2 and a heavy chain amino acid sequence of SEQ ID NO:6.

5. The method of claim 1 wherein said antibody is a RAB9 antibody, which is characterized by a light chain amino acid sequence of SEQ ID NO: 1 and a heavy chain amino acid sequence of SEQ ID NO:5.

6. The method of claim 1 wherein said antibody is a RAB0 antibody, which is characterized by a light chain amino acid sequence of SEQ ID NO: 3 and a heavy chain amino acid sequence of SEQ ID NO:7.

7. A composition comprising an anti-MIF antibody, wherein said antibody is selected from the group consisting of:
   a) a RAB4 antibody, characterized by a light chain sequence as deposited by way of plasmid deposition with deposit number DSM 25110 and a heavy chain sequence as deposited by way of plasmid deposition with deposit number DSM 25112,
   b) a RAB9 antibody, characterized by a light chain sequence as deposited by way of plasmid deposition with deposit number DSM 25111 and a heavy chain sequence as deposited by way of plasmid deposition with deposit number DSM 25113, and
   c) a RAB0 antibody, characterized by a light chain sequence as deposited by way of plasmid deposition with deposit number DSM 25114 and a heavy chain sequence as deposited by way of plasmid deposition with deposit number DSM 25115.

8. A composition comprising an anti-MIF antibody, wherein said antibody is selected from the group consisting of:
   a) a RAB4 antibody, which is characterized by a light chain amino acid sequence of SEQ ID NO: 2 and a heavy chain amino acid sequence of SEQ ID NO:6,
   b) a RAB9 antibody, which is characterized by a light chain amino acid sequence of SEQ ID NO: 1 and a heavy chain amino acid sequence of SEQ ID NO:5, and
   c) a RAB0 antibody, which is characterized by a light chain amino acid sequence of SEQ ID NO: 3 and a heavy chain amino acid sequence of SEQ ID NO:7.

9. The composition of claim 8, wherein said antibody is a RAB4 antibody, which is characterized by a light chain amino acid sequence of SEQ ID NO: 2 and a heavy chain amino acid sequence of SEQ ID NO:6.

10. The composition of claim 8, wherein said antibody is a RAB9 antibody, which is characterized by a light chain amino acid sequence of SEQ ID NO: 1 and a heavy chain amino acid sequence of SEQ ID NO:5.

11. The composition of claim 8, wherein said antibody is a RAB0 antibody, which is characterized by a light chain amino acid sequence of SEQ ID NO: 3 and a heavy chain amino acid sequence of SEQ ID NO:7.

* * * * *